US007597892B2

(12) United States Patent
Van de Winkel et al.

(10) Patent No.: US 7,597,892 B2
(45) Date of Patent: *Oct. 6, 2009

(54) METHOD FOR TREATING PSORIASIS BY ADMINISTERING HUMAN ANTIBODIES SPECIFIC FOR INTERLEUKIN 15 (IL-15)

(75) Inventors: Jan G. J. Van de Winkel, Zeist (NL); Marcus Antonius Van Dijk, Bilthoven (NL); Janine Schuurman, Amsterdam (NL); Arnout F. Gerritsen, Bunnik (NL); Ole Baadsgaard, Hellerup (DK); Jørgen Petersen, Rungsted Kyst (DK)

(73) Assignee: Genmab A/S, Copenhagen (DK)

( * ) Notice: Subject to any disclaimer, the term of this patent is extended or adjusted under 35 U.S.C. 154(b) by 263 days.

This patent is subject to a terminal disclaimer.

(21) Appl. No.: 11/827,306

(22) Filed: Jul. 11, 2007

(65) Prior Publication Data

US 2008/0166347 A1    Jul. 10, 2008

Related U.S. Application Data

(60) Division of application No. 10/379,741, filed on Mar. 5, 2003, now Pat. No. 7,247,304, which is a continuation-in-part of application No. 10/374,932, filed on Feb. 26, 2003, now Pat. No. 7,329,405, which is a continuation-in-part of application No. 10/226,615, filed on Aug. 23, 2002, now Pat. No. 7,153,507.

(60) Provisional application No. 60/314,731, filed on Aug. 23, 2001.

(51) Int. Cl.
    *A61K 39/395* (2006.01)

(52) U.S. Cl. ..................................... 424/145.1; 514/885

(58) Field of Classification Search ........................ None
See application file for complete search history.

(56) References Cited

U.S. PATENT DOCUMENTS

| | | | |
|---|---|---|---|
| 5,591,630 | A | 1/1997 | Anderson et al. |
| 5,660,824 | A | 8/1997 | Grabstein et al. |
| 5,798,966 | A | 8/1998 | Keeney |
| 6,001,973 | A | 12/1999 | Strom et al. |
| 6,075,181 | A | 6/2000 | Kucherlapati et al. |
| 6,083,477 | A | 7/2000 | Goldenberg |
| 6,114,598 | A | 9/2000 | Kucherlapati et al. |
| 6,165,466 | A | 12/2000 | Grabstein et al. |
| 6,184,359 | B1 | 2/2001 | Grabstein et al. |
| 6,258,352 | B1 | 7/2001 | Shimonaka |
| 6,632,927 | B2 | 10/2003 | Adair et al. |
| 7,247,304 | B2 | 7/2007 | van de Winkel et al. |
| 2002/0182178 | A1 | 12/2002 | Grooten et al. |

FOREIGN PATENT DOCUMENTS

| | | |
|---|---|---|
| CA | 2232813 | 4/1997 |
| EP | 1273304 A2 | 1/2003 |
| EP | 1273304 A3 | 1/2003 |
| JP | 11-500908 | 1/1999 |
| WO | WO-96/34096 A1 | 10/1996 |
| WO | WO-98/37757 A1 | 9/1998 |
| WO | WO-99/45962 A1 | 9/1999 |
| WO | WO-00/02582 A2 | 1/2000 |
| WO | WO-00/02582 A3 | 1/2000 |
| WO | WO-01/02003 A1 | 1/2001 |
| WO | WO-02/22805 A2 | 3/2002 |
| WO | WO-03/017935 A2 | 3/2003 |
| WO | WO-2004/076620 A2 | 9/2004 |

OTHER PUBLICATIONS

Casset, Florence et al., "A peptide mimetic of an anti-CD4 monoclonal antibody by rational design," *Biochemical and Biophysical Research Communications*, vol. 307:198-205 (2003).

Chen, Yvonne et al., "Selection and Analysis of an Optimized Anti-VEGF Antibody: Crystal Structure of an Affinity-matured Fab in Complex with Antigen," *J. Mol. Biol.*, vol. 293:865-881 (1999).

De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," *The Journal of Immunology*, vol. 169:3076-3084 (2002).

Holm, Patrik et al., "Functional mapping and single chain construction of the anti-cytokeratin 8 monoclonal antibody TS1," *Molecular Immunology*, vol. 44:1075-1084 (2007).

MacCallum, Robert M. et al., "Antibody-antigen Interactions: Contact Analysis and Binding Site Topography," *J. Mol. Biol.*, vol. 262:732-745 (1996).

Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).

Wu, Herren et al., "Humanization of a Murine Monoclonal Antibody by Simultaneous Optimization of Framework and CDR Residues," *J. Mol. Biol.*, vol. 294:151-162 (1999).

Canadian Office Action for Application No. 2456648, dated Nov. 19, 2007.

Amit, A.G. et al., "Three-Dimensional Structure of an Antigen-Antibody Complex at 2.8 Å Resolution," *Science*, vol. 233:747-753 (1986).

Bentley, David L., "Most κ immunoglobulin mRNA in human lymphocytes is homologous to a small family of germ-line V genes," *Nature*, vol. 307(5946):77-80 (1984).

(Continued)

*Primary Examiner*—Prema Mertz
(74) *Attorney, Agent, or Firm*—Jane E. Remillard; Jeanne M. DiGiorgio; Lahive & Cockfield LLP

(57) ABSTRACT

Isolated human monoclonal antibodies which specifically bind to IL-15 (e.g., human IL-15), and related antibody-based compositions and molecules, are disclosed. The human antibodies can be produced in a transfectoma or in a non-human transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, non-human transgenic animals, and hybridomas which produce the human antibodies, and therapeutic and diagnostic methods for using the human antibodies.

13 Claims, 19 Drawing Sheets

OTHER PUBLICATIONS

Davies, Julian et al., "Affinity improvement of single antibody VH domains: residues in all three hypervariable regions affect antigen binding," *Immunotechnology*, vol. 2:169-179 (1996).

Kipps, Thomas J. et al., "Autoantibody-Associated κ Light Chain Variable Region Gene Expressed in Chronic Lymphocytic Leukemia with Little or No Somatic Mutation," *J. Exp. Med.*, vol. 167:840-852 (1988).

Panka, David J. et al., "Variable region framework differences result in decreased or increased affinity of variant anti-digoxin antibodies," *Proc. Natl. Acad Sci. USA*, vol. 85:3080-3084 (1988).

Rudikoff, Stuart et al., "Single amino acid substitution altering antigen-binding specificity," *Proc. Natl. Acad. Sci. USA*, vol. 79:1979-1983 (1982).

Stausberg, R.L. et al., "Generation and initial analysis of more than 15,000 full-length human and mouse cDNA sequences," *PNAS*, vol. 99(26):16899-16903 (2002).

The Merck Manual of Diagnosis and Therapy, 17th Edition, Mark H. Beers and Robert Berkow, Eds., Merck Research Laboratories, pp. 165-177 and pp. 986-995 (1999).

Villadsen, Louise S. et al., "Resolution of psoriasis upon blockade of IL-15 biological activity in a xenograft mouse model," *The Journal of Clinical Investigation*, vol. 112(10):1571-1580 (2003).

Fehniger, Todd A. et al., "Interleukin 15: biology and relevance to human disease," *Blood*, vol. 97(1):14-32 (2001).

McInnes, Iain B. et al., "Interleukin-15 mediates T cell-dependent regulation of tumor necrosis factor-α production in rheumatoid arthritis," *Nature Medicine*, vol. 3(2):189-195 (1997).

European Search Report for Application No. 02796411.3-2402, dated Jul. 4, 2007.

Pettit, Dean K. et al., "Structure-Function Studies of Interleukin 15 using Site-specific Mutagenesis, Polyethylene Glycol Conjugation, and Homology Modeling," *The Journal of Biological Chemistry*, vol. 272(4):2312-2318 (1997).

Waldmann, Thomas A. et al., "Contrasting Roles of IL-2 and IL-15 in the Life and Death of Lymphocytes: Implications and Immunotherapy," *Immunity*, vol. 14:105-110 (2001).

146B7 VK

```
AB11 GAA ATT GTG TTG ACG CAG TCT CCA GGC ACC CTG TCT TTG TCT CCA GGG GAA AGA GCC ACC  60
     E   I   V   L   T   Q   S   P   G   T   L   S   L   S   P   G   E   R   A   T  *
                                      FR1                                            T>

CTC TCC TGC AGG GCC AGT CAG AGT GTT AGC AGC TAC TTA GCC TGG TAC CAG CAG AAA      120
     L   S   C   R   A   S   Q   S   V   S   S   S   Y   L   A   W   Y   Q   Q   K   *
                         ━━━━━━━━━━━━━━━━━━━━━━━━━━━━━━━━━━━                          K>
                                      CDR1

CCT GGC CAG GCT CCC AGG CTC CTC ATC TAT GGT GCA TCC CGC AGG GCC ACT GGC ATC CCA  180
     P   G   Q   A   P   R   L   L   I   Y   G   A   S   R   R   A   T   G   I   P   *
                                              A                                       P>
                                              ━━━━━━━━━━━━━━━
                                                  CDR2

GAC AGG TTC AGT GGC AGT GGG TCT GGG ACA GAC TTC ACT CTC ACC ATC AGC AGA CTG GAG  240
     D   R   F   S   G   S   G   S   G   T   D   F   T   L   T   I   S   R   L   E   *
                             FR2                                                      E>

CCT GAA GAT TTT GCA GTG TAT TAC TGT CAG CAG TAT GGT AGC TAT CCT ACT TTT GGC CAG  300
     P   E   D   F   A   V   Y   Y   C   Q   Q   Y   G   S   Y   P   T   F   G   Q   *
                                              A   R                                   Q>
                                              ━━━━━━━━━━━━━━━━━━━
                                                    CDR3

GGG ACC AAG CTG GAG ATC AAG CGA ACT GTG GCT GCA CCA TCT GTC TTC ATC TTC CCG AB16
     G   T   K   L   E   I   K   R   T   V   A   A   P   S   V   F   I   F   P
                                      AA                 ▲                            P>
                                                   K constant
                   FR4                     ▲Jκ2
```

FIG. 3

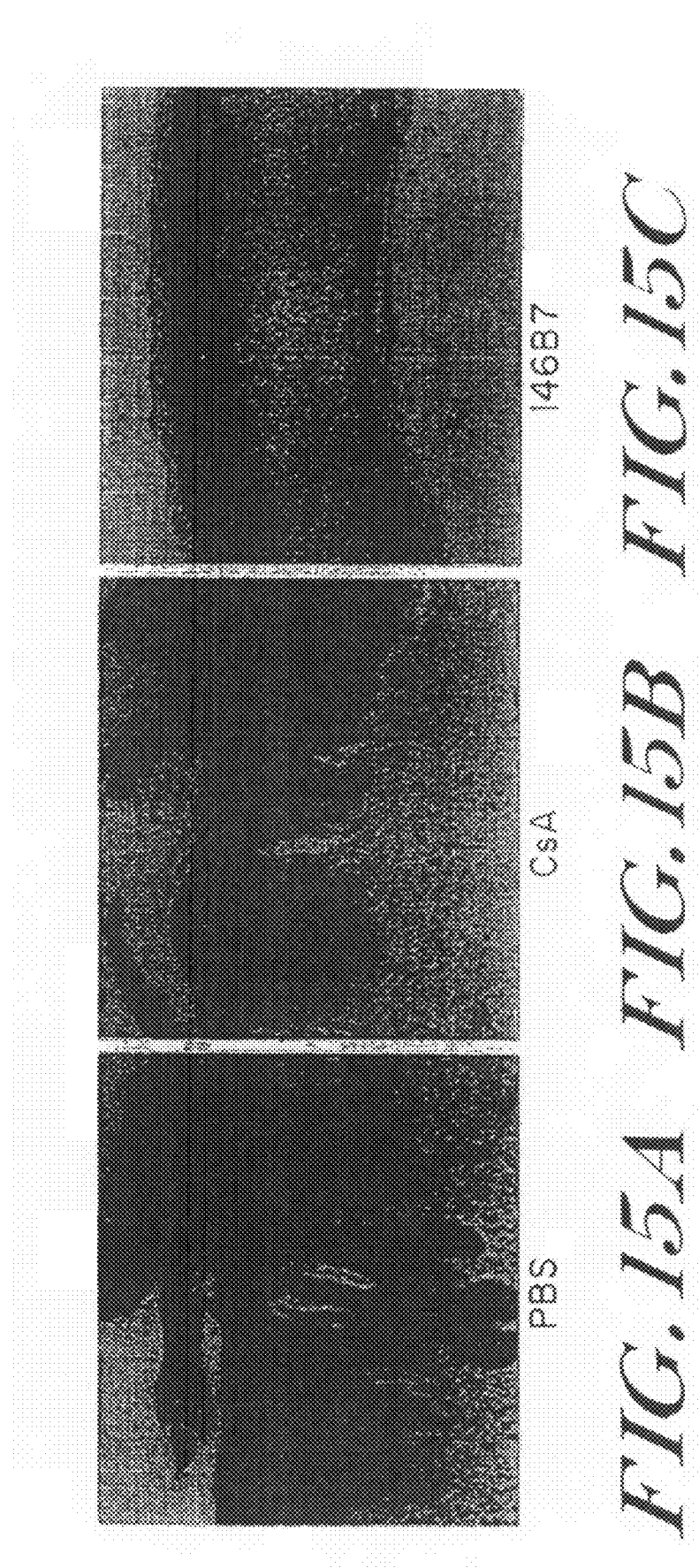

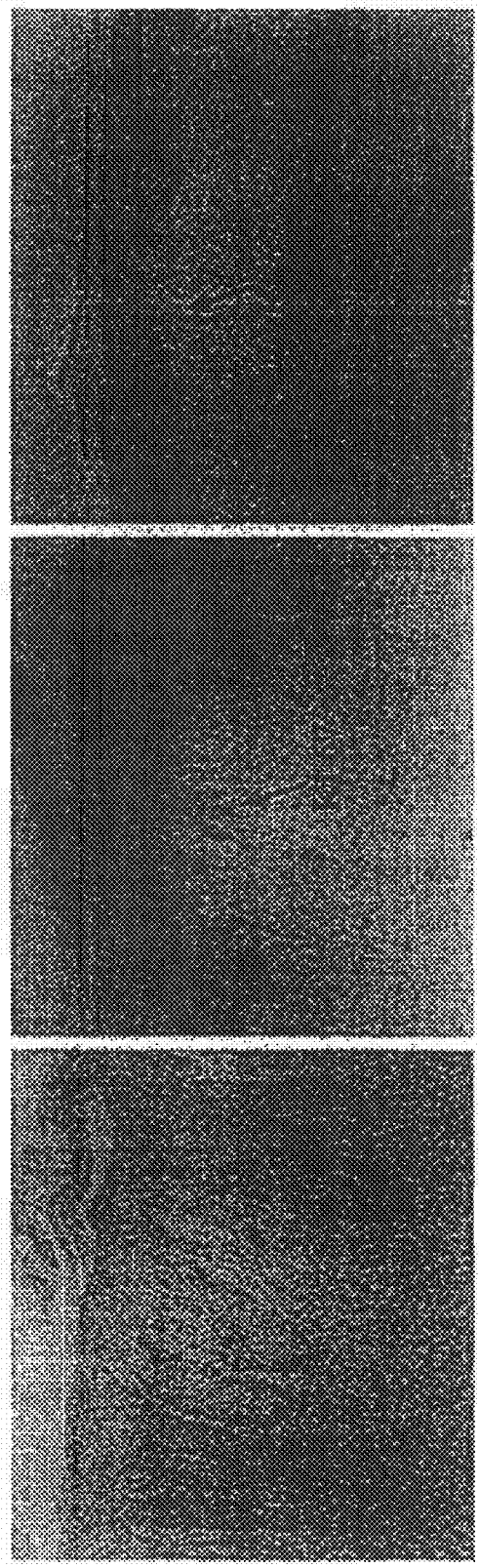

SEQUENCE LISTING

```
<160> NUMBER OF SEQ ID NOS: 31

<210> SEQ ID NO 1
<211> LENGTH: 390
<212> TYPE: DNA
<213> ORGANISM: Homo sapiens
<220> FEATURE:
<221> NAME/KEY: CDS
<222> LOCATION: (1)...(390)

<400> SEQUENCE: 1 gag gtg cag ctg gtg cag tct gga gca gag gtg aaa aag ccc ggg gag      48
Glu Val Gln Leu Val Gln Ser Gly Ala Glu Val Lys Lys Pro Gly Glu
 1               5                  10                  15 tct ctg aag atc tcc tgt aag gtt tct gga tac ttc ttt acc acc tac      96
Ser Leu Lys Ile Ser Cys Lys Val Ser Gly Tyr Phe Phe Thr Thr Tyr
             20                  25                  30 tgg atc ggc tgg gtg cgc cag atg ccc ggg aaa ggc ctg gag tat atg     144
Trp Ile Gly Trp Val Arg Gln Met Pro Gly Lys Gly Leu Glu Tyr Met
         35                  40                  45 ggg atc atc tat cct ggt gac tct gat acc aga tac agc ccg tcc ttc     192
Gly Ile Ile Tyr Pro Gly Asp Ser Asp Thr Arg Tyr Ser Pro Ser Phe
     50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                 85                  90                  95 gcg aga ggg ggt aac tgg aac tgc ttt gac tac tgg ggc cag gga acc     336
Ala Arg Gly Gly Asn Trp Asn Cys Phe Asp Tyr Trp Gly Gln Gly Thr
            100                 105                 110 ctg gtc acc gtc tcc tca gcc tcc acc aag ggc cca tcg gtc ttc ccc     384
Leu Val Thr Val Ser Ser Ala Ser Thr Lys Gly Pro Ser Val Phe Pro
        115                 120                 125 ctg gca                                                              390
Leu Ala
    130

<210> SEQ ID NO 2
<211> LENGTH: 130
<212> TYPE: PRT
<213> ORGANISM: Homo sapiens

<400> SEQUENCE: 2

Glu Val Gln Leu Val Gln Ser Gly Ala Glu Val Lys Lys Pro Gly Glu
 1               5                  10                  15

Ser Leu Lys Ile Ser Cys Lys Val Ser Gly Tyr Phe Phe Thr Thr Tyr
             20                  25                  30

Trp Ile Gly Trp Val Arg Gln Met Pro Gly Lys Gly Leu Glu Tyr Met
         35                  40                  45
```

```
Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Asn Trp Asn Cys Phe Asp Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala
    130

<210> SEQ ID NO 3
<211> LENGTH: 357
<212> TYPE: DNA
<213> ORGANISM: Homo sapiens
<220> FEATURE:
<221> NAME/KEY: CDS
<222> LOCATION: (1)...(357)

<400> SEQUENCE: 3 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc cgc agg gcc act ggc atc cca gac agg ttc agt     192
Ile Tyr Gly Ala Ser Arg Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cgg tat ggt agc tca cac     288
Pro Glu Asp Phe Ala Val Tyr Tyr Cys Gln Arg Tyr Gly Ser Ser His
                 85                  90                  95 act ttt ggc cag ggg acc aag ctg gag atc agc cga act gtg gct gca     336
Thr Phe Gly Gln Gly Thr Lys Leu Glu Ile Ser Arg Thr Val Ala Ala
                100                 105                 110 cca tct gtc ttc atc ttc ccg                                         357
Pro Ser Val Phe Ile Phe Pro
        115

<210> SEQ ID NO 4
<211> LENGTH: 119
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
```

```
                50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Arg Tyr Gly Ser Ser His
                 85                  90                  95

Thr Phe Gly Gln Gly Thr Lys Leu Glu Ile Ser Arg Thr Val Ala Ala
                100                 105                 110

Pro Ser Val Phe Ile Phe Pro
        115

<210> SEQ ID NO 5
<211> LENGTH: 5
<212> TYPE: PRT
<213> ORGANISM: Homo sapiens

<400> SEQUENCE: 5

Thr Tyr Trp Ile Gly
 1               5

<210> SEQ ID NO 6
<211> LENGTH: 17
<212> TYPE: PRT
<213> ORGANISM: Homo sapiens

<400> SEQUENCE: 6

Ile Ile Tyr Pro Gly Asp Ser Asp Thr Arg Tyr Ser Pro Ser Phe Gln
 1               5                  10                  15

Gly

<210> SEQ ID NO 7
<211> LENGTH: 8
<212> TYPE: PRT
<213> ORGANISM: Homo sapiens

<400> SEQUENCE: 7

Gly Asn Trp Asn Cys Phe Asp Tyr
 1               5

<210> SEQ ID NO 8
<211> LENGTH: 12
<212> TYPE: PRT
<213> ORGANISM: Homo sapiens

<400> SEQUENCE: 8

Arg Ala Ser Gln Ser Val Ser Ser Ser Tyr Leu Ala
 1               5                  10

<210> SEQ ID NO 9
<211> LENGTH: 7
<212> TYPE: PRT
<213> ORGANISM: Homo sapiens

<400> SEQUENCE: 9

Gly Ala Ser Arg Arg Ala Thr
 1               5

<210> SEQ ID NO 10
<211> LENGTH: 8
<212> TYPE: PRT
<213> ORGANISM: Homo sapiens

<400> SEQUENCE: 10
```

```
Gln Arg Tyr Gly Ser Ser His Thr
  1               5
```

<210> SEQ ID NO 11
<211> LENGTH: 20
<212> TYPE: DNA
<213> ORGANISM: Homo sapiens

<400> SEQUENCE: 11
caggtkcagc tggtgcagtc                                              20

<210> SEQ ID NO 12
<211> LENGTH: 20
<212> TYPE: DNA
<213> ORGANISM: Homo sapiens

<400> SEQUENCE: 12
saggtgcagc tgktggagtc                                              20

<210> SEQ ID NO 13
<211> LENGTH: 20
<212> TYPE: DNA
<213> ORGANISM: Homo sapiens

<400> SEQUENCE: 13
gaggtgcagc tggtgcagtc                                              20

<210> SEQ ID NO 14
<211> LENGTH: 20
<212> TYPE: DNA
<213> ORGANISM: Homo sapiens

<400> SEQUENCE: 14
atggactgga cctggagcat                                              20

<210> SEQ ID NO 15
<211> LENGTH: 21
<212> TYPE: DNA
<213> ORGANISM: Homo sapiens

<400> SEQUENCE: 15
catggaattg gggctgagct g                                            21

<210> SEQ ID NO 16
<211> LENGTH: 20
<212> TYPE: DNA
<213> ORGANISM: Homo sapiens

<400> SEQUENCE: 16
atggagtttg grctgagctg                                              20

<210> SEQ ID NO 17
<211> LENGTH: 21
<212> TYPE: DNA
<213> ORGANISM: Homo sapiens

<400> SEQUENCE: 17
atgaaacacc tgtggttctt c                                            21

<210> SEQ ID NO 18
<211> LENGTH: 20
<212> TYPE: DNA
<213> ORGANISM: Homo sapiens

```
<400> SEQUENCE: 18
atggggtcaa ccgccatcct                                              20

<210> SEQ ID NO 19
<211> LENGTH: 21
<212> TYPE: DNA
<213> ORGANISM: Homo sapiens

<400> SEQUENCE: 19
tgccaggggg aagaccgatg g                                            21

<210> SEQ ID NO 20
<211> LENGTH: 20
<212> TYPE: DNA
<213> ORGANISM: Homo sapiens

<400> SEQUENCE: 20
racatccaga tgayccagtc                                              20

<210> SEQ ID NO 21
<211> LENGTH: 20
<212> TYPE: DNA
<213> ORGANISM: Homo sapiens

<400> SEQUENCE: 21
gycatcyrga tgacccagtc                                              20

<210> SEQ ID NO 22
<211> LENGTH: 20
<212> TYPE: DNA
<213> ORGANISM: Homo sapiens

<400> SEQUENCE: 22
gatattgtga tgacccagac                                              20

<210> SEQ ID NO 23
<211> LENGTH: 20
<212> TYPE: DNA
<213> ORGANISM: Homo sapiens

<400> SEQUENCE: 23
gaaattgtgt tgacrcagtc                                              20

<210> SEQ ID NO 24
<211> LENGTH: 20
<212> TYPE: DNA
<213> ORGANISM: Homo sapiens

<400> SEQUENCE: 24
gaaatwgtra tgacacagtc                                              20

<210> SEQ ID NO 25
<211> LENGTH: 20
<212> TYPE: DNA
<213> ORGANISM: Homo sapiens

<400> SEQUENCE: 25
gatgttgtga tgacacagtc                                              20

<210> SEQ ID NO 26
<211> LENGTH: 20
<212> TYPE: DNA
<213> ORGANISM: Homo sapiens
```

```
<400> SEQUENCE: 26
gaaattgtgc tgactcagtc                                              20

<210> SEQ ID NO 27
<211> LENGTH: 24
<212> TYPE: DNA
<213> ORGANISM: Homo sapiens

<400> SEQUENCE: 27
cccgctcagc tcctggggct cctg                                         24

<210> SEQ ID NO 28
<211> LENGTH: 23
<212> TYPE: DNA
<213> ORGANISM: Homo sapiens

<400> SEQUENCE: 28
ccctgctcag ctcctggggc tgc                                          23

<210> SEQ ID NO 29
<211> LENGTH: 26
<212> TYPE: DNA
<213> ORGANISM: Homo sapiens

<400> SEQUENCE: 29
cccagcgcag cttctcttcc tcctgc                                       26

<210> SEQ ID NO 30
<211> LENGTH: 27
<212> TYPE: DNA
<213> ORGANISM: Homo sapiens

<400> SEQUENCE: 30
atggaaccat ggaagcccca gcacagc                                      27

<210> SEQ ID NO 31
<211> LENGTH: 20
<212> TYPE: DNA
<213> ORGANISM: Homo sapiens

<400> SEQUENCE: 31
cgggaagatg aagacagatg                                              20
```

METHOD FOR TREATING PSORIASIS BY ADMINISTERING HUMAN ANTIBODIES SPECIFIC FOR INTERLEUKIN 15 (IL-15)

RELATED APPLICATIONS

This application is a divisional of continuation application Ser. No. 10/379,741, entitled "Human Antibodies Specific for Interleukin 15 (IL-15)", filed Mar. 5, 2003, which will issue as U.S. Pat. No. 7,724,304 on Jul. 24, 2007, which is a continuation of prior filed application Ser. No. 10/374,932, entitled "Human Antibodies Specific for Interleukin 15 (IL-15)", filed on Feb. 26, 2003, which is a continuation-in-part of issued U.S. Pat. No. 7,153,507, issued on Dec. 26, 2006, entitled "Human Antibodies Specific for Interleukin 15 (IL-15)", filed on Aug. 23, 2002, which claims priority to U.S. Provisional Application No. 60/314,731 entitled "Human Antibodies Specific for Interleukin 15 (IL-15)", filed on Aug. 23, 2001, the contents of which are incorporated herein by reference.

BACKGROUND OF THE INVENTION

Interleukin-15 (IL-15) is a pro-inflammatory cytokine, a glycoprotein of 14-15 kD. Constitutive expression has been reported in various cells and tissues including monocytes and macrophages, fibroblasts, keratinocytes and dendritic cells (Waldmann and Tagaya, 1999; Fehniger and Caligiuri, 2001). The expression is upregulated under inflammatory conditions, as reported for monocytes stimulated with IFN-γ and LPS or by infection with viruses, bacteria or protozoans (Kirman et al., 1998; Waldmann et al., 1998; Waldmann and Tagaya, 1999; Fehniger and Caligiuri, 2001). Furthermore, in chronic inflammatory diseases such as rheumatoid arthritis, locally produced IL-15 is likely to amplify inflammation by the recruitment and activation of synovial T-cells. This IL-15-induced effect has been suggested to play a pivotal role in disease pathogenesis (Kirman et al., 1998; McInnes et al., 1996; McInnes et al., 1997; McInnes and Liew, 1998; Fehniger and Caligiuri, 2001).

In vitro studies have shown that IL-15 shares several biological activities with IL-2, due to shared receptor components. The IL-15 receptor present on T-cells consists of an unique α-chain, IL-15Rα, but shares the β-chain and the γ-chain with IL-2R. As a consequence, both receptors use the same Jak/STAT-signaling elements. However, based on complex regulation and differential expression of IL-2 and IL-15 and their receptors, critical differences in the in vivo functions have been reported (Kirman et al., 1998; Waldmann and Tagaya, 1999; Waldmann et al., 2001). It is also important to note the non-redundant role for IL-15 in natural killer (NK) cell, NK-T cell and intraepithelial lymphocyte development, survival, expansion and function (Kennedy et al., 2000; Liu et al., 2000).

McInnes and coworkers (McInnes et al., 1997; McInnes and Liew, 1998) reported the induction of TNF-α production after IL-15 stimulation in T-cells derived from rheumatoid arthritis patients. Furthermore, peripheral blood T cells activated by IL-15 were shown to induce significant TNF-α production by macrophages via a cell-contact-dependent mechanism. Because of the destructive role of TNF-α in rheumatoid arthritis, inhibition of this cytokine decreases disease activity (Bathon et al., 2000; Klippel, 2000; Lovell et al., 2000; Maini and Taylor, 2000).

SUMMARY OF THE INVENTION

The present invention is based on the generation and isolation, for the first time, of fully human monoclonal antibodies which specifically bind to human IL-15 and which inhibit the proinflammatory effects induced by IL-15, as well as the characterization of such novel antibodies and the demonstration of their therapeutic value in treating a variety of IL-15 mediated diseases. For example, as described herein, the human antibodies have been shown to inhibit both TNFα production and T cell proliferation, both of which are integrally involved in inflammatory disorders. Accordingly, the human antibodies of the present invention provide an improved means for treating and preventing such disorders (and any other IL-15 mediated disorder), attributable in part to their unique specificity (e.g., epitope and species specificity), affinity, structure, functional activity and the fact that they are fully human, making them significantly less immunogenic and more therapeutically effective and useful when administered to human patients than other IL-15 antibodies previously generated (e.g., murine and humanized antibodies). The present invention is also based on the discovery of new therapeutic applications, including treatment of inflammatory diseases, such as rheumatoid arthritis, psoriasis, transplant rejections and cancers, for IL-15 inhibiting antibodies such as the human antibodies described herein.

Isolated human antibodies of the invention include a variety of antibody isotypes, such as IgG1, IgG2, IgG3, IgG4, IgM, IgA1, IgA2, IgAsec, IgD, and IgE. Typically, they include IgG1 (e.g., IgG1k), IgG3 and IgM isotypes. The antibodies can be full-length (e.g., an IgG1 or IgG3 antibody) or can include only an antigen-binding portion (e.g., a Fab, F(ab')$_2$, Fv, a single chain Fv fragment, an isolated complementarity determining region (CDR) or a combination of two or more isolated CDRs).

In one embodiment, the human antibodies are recombinant antibodies. In a particular embodiment, the human antibody is encoded by human IgG heavy chain and human kappa light chain nucleic acids comprising nucleotide sequences in their variable regions as set forth in SEQ ID NO:1 and SEQ ID NO:3, respectively, and conservative sequence modifications thereof. In another embodiment, the human antibody includes IgG heavy chain and kappa light chain variable regions which comprise the amino acid sequences shown in SEQ ID NO:2 and SEQ ID NO:4, respectively, and conservative sequence modifications thereof.

Human antibodies of the invention can be produced recombinantly in a host cell, such as a transfectoma (e.g., a transfectoma consisting of immortalized CHO cells or lymphocytic cells) containing nucleic acids encoding the heavy and light chains of the antibody, or be obtained directly from a hybridoma which expresses the antibody (e.g., which includes a B cell obtained from a transgenic non-human animal, e.g., a transgenic mouse, having a genome comprising a human heavy chain transgene and a human light chain transgene that encode the antibody, fused to an immortalized cell). In a particular embodiment, the antibodies are produced by a hybridoma referred to herein as 146B7 or by a host cell (e.g., a CHO cell) transfectoma containing human heavy chain and human light chain nucleic acids which comprise nucleotide sequences in their variable regions as set forth in SEQ ID NOs: 1 and 3, respectively, and conservative modifications thereof. In particular embodiments, the antibodies are produced by hybridomas referred to herein as 146B7, 146H5, 404E4, and 404A8. In a preferred embodiment, the antibody specifically binds to an epitope located on the β- and/or γ-chain interacting domain of IL-15.

In another embodiment, the human antibodies of the present invention specifically bind to human IL-15 and inhibit the ability of IL-15 to induce proinflammatory effects, e.g., inhibit the production of TNFα and/or inhibit the proliferation of T cells, such as PBMC or CTLL-2 T cells, upon IL-15 binding to the IL-15 receptor. Typically, the human antibodies bind to IL-15 with a dissociation equilibrium constant ($K_D$) of less than approximately $10^{-7}$ M, such as less than approximately $10^{-8}$ M, $10^{-9}$ M or $10^{-10}$ M or even lower when determined by surface plasmon resonance (SPR) technology in a BIACORE 3000 instrument using recombinant human IL-15 as the analyte and the antibody as the ligand. In a particular embodiment, the antibody binds to human IL-15 with a dissociation equilibrium constant ($K_D$) of approximately $6.5 \times 10^{-8}$ M.

In a further embodiment, the invention relates to an isolated human monoclonal antibody which specifically binds to human IL-15, comprising at least one CDR sequence selected from the group consisting of:

(i) SEQ ID NOs: 5, 6, 7, 8, 9, and 10;

(ii) sequences which are at least 90% homologous, preferably at least 95% homologous, and more preferably at least 98%, or at least 99% homologous to the sequences defined in (i); and (iii) fragments of the sequences defined in (i) or (ii), which retain the ability to specifically bind to human IL-15.

In a further embodiment, the invention relates to an isolated human monoclonal antibody which specifically binds to human IL-15 comprising (i) SEQ ID NO:7;

(ii) a sequence which is at least 90% homologous, preferably at least 95% homologous, and more preferably at least 98%, or at least 99% homologous to SEQ ID NO:7; or (iii) a fragment of the sequence defined in (i) or (ii), which retains the ability to specifically bind to human IL-15.

In a further embodiment, the invention relates to an isolated human monoclonal antibody which specifically binds to human IL-15, comprising (i) SEQ ID NOs:5 and 8;

(ii) SEQ ID NOs:6 and 9;

(iii) SEQ ID NOs:7 and 10;

(iv) sequences which are at least 90% homologous, preferably at least 95% homologous, and more preferably at least 98%, or at least 99% homologous to the sequences defined in (i), (ii) or (iii); or (v) fragments of the sequences defined in (i), (ii), (iii) or (iv), which retain the ability to specifically bind to human IL-15.

In a further embodiment, the invention relates to an isolated human monoclonal antibody which specifically binds to human IL-15, comprising at least four CDRs selected from (i) SEQ ID NOs:5, 6, 7, 8, 9, or 10;

(ii) sequences which are at least 90% homologous, preferably at least 95% homologous, and more preferably at least 98%, or at least 99% homologous to the sequences defined in (i); and (iii) fragments of the sequences defined in (i) or (ii), which retain the ability to specifically bind to human IL-15.

In a further embodiment, the invention relates to an isolated human monoclonal antibody which specifically binds to human IL-15, comprising (i) SEQ ID NOs:5, 6, 7, 8, 9, or 10;

(ii) sequences which are at least 90% homologous, preferably at least 95% homologous, and more preferably at least 98%, or at least 99% homologous to the sequences defined in (i); or (iii) fragments of the sequences defined in (i) or (ii), which retain the ability to specifically bind to human IL-15.

In a further embodiment, the invention relates to an isolated human monoclonal antibody which specifically binds to human IL-15, comprising a heavy chain variable region with amino acid sequence SEQ ID NO:2; or a sequence which is at least 90% homologous, preferably at least 95% homologous, and more preferably at least 98%, or at least 99% homologous with SEQ ID NO:2.

In a further embodiment, the invention relates to an isolated human monoclonal antibody which specifically binds to human IL-15, comprising a light chain variable region with amino acid sequence SEQ ID NO:4; or a sequence which is at least 90% homologous, preferably at least 95% homologous, and more preferably at least 98%, or at least 99% homologous with SEQ ID NO:4.

In a further embodiment, the invention relates to an isolated human monoclonal antibody which specifically binds to human IL-15, which inhibits cis-signalling via the IL-15Rγ-chain by specifically binding to an epitope located on the γ-chain interacting domain of human IL-15, and which inhibits trans-signalling on neighboring cells expressing the γ-chain or the β- and γ-chains as part of IL-15R or another cytokine receptor.

In yet another embodiment, the isolated human monoclonal antibody specifically binds to human IL-15 and interferes with IL-15 receptor α-, β- and γ-chain assembly and/or inhibits assembly on neighboring cells expressing β- and γ-chains as part of the IL-15 receptor or another cytokine receptor.

In another aspect, the invention provides nucleic acid molecules encoding the antibodies, or antigen-binding portions, of the invention. Accordingly, recombinant expression vectors which include the antibody-encoding nucleic acids of the invention, and host cells transfected with such vectors, are also encompassed by the invention, as are methods of making the antibodies of the invention by culturing these host cells.

The invention also relates to an expression vector comprising a nucleotide sequence encoding heavy and light variable regions which comprise the amino acid sequences shown in SEQ ID NO:2 and SEQ ID NO:4, respectively, and conservative modifications thereof. Such expression vectors are well known in the art. Examples hereof include in vitro transcription/translation vectors using, for example, reticulocyte lysates.

In yet another aspect, the invention provides isolated B-cells from a transgenic non-human animal, e.g., a transgenic mouse, which are capable of expressing various isotypes (e.g., IgG, IgA and/or IgM) of human monoclonal antibodies that specifically bind to IL-15. Preferably, the isolated B cells are obtained from a transgenic non-human animal, e.g., a transgenic mouse, which has been immunized with a purified or enriched preparation of IL-15 antigen and/or cells expressing IL-15. Preferably, the transgenic non-human animal, e.g., a transgenic mouse, has a genome comprising a human heavy chain transgene and a human light chain transgene. The isolated B-cells are then immortalized to provide a source (e.g., a hybridoma) of human monoclonal antibodies to IL-15.

Accordingly, the present invention also provides a hybridoma capable of producing human monoclonal antibodies that specifically bind to IL-15. In one embodiment, the hybridoma includes a B cell obtained from a transgenic non-human animal, e.g., a transgenic mouse, having a genome comprising a human heavy chain transgene and a human light chain transgene fused to an immortalized cell. The transgenic non-human animal can be immunized with a purified or enriched preparation of IL-15 antigen and/or cells expressing IL-15 to generate antibody-producing hybridomas. Particular hybridomas provided by the invention include 146B7, 146H5, 404E4, and 404A8.

In yet another aspect, the invention provides a transgenic non-human animal, such as a transgenic mouse, which expresses human monoclonal antibodies that specifically bind to IL-15. In a particular embodiment, the transgenic non-human animal is a transgenic mouse having a genome comprising a human heavy chain transgene and a human light chain transgene. The transgenic non-human animal can be immunized with a purified or enriched preparation of IL-15 antigen and/or cells expressing IL-15. Preferably, the transgenic non-human animal, e.g., the transgenic mouse, is capable of producing multiple isotypes of human monoclonal antibodies to IL-15 (e.g., IgG, IgA and/or IgM) by undergoing V-D-J recombination and isotype switching. Isotype switching may occur by, e.g., classical or non-classical isotype switching.

In another aspect, the present invention provides methods for producing human monoclonal antibodies which specifically react with IL-15. In one embodiment, the method includes immunizing a transgenic non-human animal, e.g., a transgenic mouse, having a genome comprising a human heavy chain transgene and a human light chain transgene, with a purified or enriched preparation of IL-15 antigen and/or cells expressing IL-15. B cells (e.g., splenic B cells) of the animal are then obtained and fused with myeloma cells to form immortal, hybridoma cells that secrete human monoclonal antibodies against IL-15.

In another aspect, the present invention features a human anti-IL-15 antibody conjugated to a therapeutic moiety, e.g., a cytotoxic drug, an enzymatically active toxin, or a fragment thereof, a radioisotope, or a small molecule anti-cancer drug.

In another aspect, the present invention provides compositions, e.g., pharmaceutical and diagnostic compositions, comprising a pharmaceutically acceptable carrier and at least one human monoclonal antibody of the invention which specifically binds to IL-15. The composition can further include other therapeutic agents, such as other immunosuppressive agents, or chemotherapeutic agents.

In yet another aspect, the invention provides methods for inhibiting the proinflammatory effects of IL-15, such as inhibiting IL-15 induced TNFα production and/or T cell proliferation, preferably without inhibiting the activity (e.g., TNFα production and/or T cell proliferation) of structurally related proteins/cytokines (e.g., IL-2) using one or more human antibodies of the invention.

Human antibodies of the present invention can be used to treat and/or prevent a variety of IL-15 mediated diseases by administering the antibodies to patients suffering from such diseases.

Exemplary diseases that can be treated (e.g., ameliorated) or prevented using the methods and compositions of the invention include, but are not limited to, inflammatory disorders, such as arthritis (e.g., psoriatic arthritis and rheumatoid arthritis including active rheumatoid arthritis and juvenile rheumatoid arthritis), inflammatory bowel disease. For example, the antibodies have been shown to reduce parakeratosis, reduce epidermal thickness and reduce proliferation of keratinocytes in psoriasis. The antibodies also have been shown to reduce inflammation and/or prevent chemotaxis of activated leukocytes involved in rheumatoid arthritis. The antibodies also can be used to treat infectious diseases, such as HIV infection. Furthermore, the antibodies can be used to treat transplant rejection. Accordingly, the human monoclonal antibodies of the invention may be useful in patients undergoing or who have undergone organ or tissue transplantation, such as heart, lung, combined heart-lung, trachea, kidney, liver, pancreas, esophagus, bowel, skin, limb transplantation, umbilical cord transplantation, stem cell transplantation, islet cell transplantation, etc.

Antibodies of the present invention may thus be used in prophylaxis of allograft and xenograft rejection or be used to reverse, treat, or otherwise ameliorate acute allograft or zenograft rejection episodes.

Further diseases that can be treated include graft-versus-host disease, e.g. blood transfusion graft-versus-host disease and bone marrow graft-versus-host disease Still further, the antibodies can be used to treat a variety of diseases involving IL-15 mediated neovascularization, such as tumor growth and cancers, e.g. T-cell leukaemia. Other examples with increased angiogenesis include inflammatory diseases, such as rheumatoid arthritis.

In a further embodiment, the invention relates to a method of treating or preventing a disorder that is associated with an overexpression of human IL-15, and/or in which a downregulation or inhibition of human IL-15 induced effects is beneficial, comprising administering the antibody according to the invention to a subject in an amount effective to treat or prevent the disorder.

In a further embodiment the disorder is selected from the group consisting of arthritides, such as ankylosing spondylitis, reactive arthritis, sacroileitis, and adult Still's disease;

connective tissue disorders, such as systemic lupus erythematosus, discoid lupus, CNS lupus, lupus nephritis, sarcoidosis, CNS sarcoidosis, and polymyositis/dermatomyositis;

opthalmological disorders, such as uveitis and choreoritinitis;

neurological disorders, such as myelopathy/tropical spastic paraparesis, myasthenia gravis, cervical uterine cancer, rhabdomyosarcoma, Ewing's sarcoma, and multiple sclerosis;

gastrointestinal and hepatic disorders, such as acute fulminant hepatitis, coeliaki, post-operative enterocolitis, ulcerative colitis, and Crohn's disease;

allergic disorders, such as bronchial asthma;

hematologic disorders, such as acute T-cell lymphoblastoid leukaemia, adult T-cell leukaemia, Sezary's syndrome, chronic lymphocytic leukaemia, mycosis fingoides, precursor B-cell acute lymphoblastic leukaemia/lymphoma, chronic myelogenous leukemia, acute myeloid leukaemia, large granular lymphocytosis, large granular lymphocyte leukaemia, myeloma, plasmacytoma, plasma cell myeloma, heavy chain diseases (including γ, μ and α disease), extranodal natural killer/T-cell lymphoma, and aggressive natural killer-cell leukemia;

skin disorders, such as allergic contact excema, bullous pemphigoid, post-burn hypertrophic scars, and lichen ruber;

pulmonary disorders, such as chronic obstructive lung disease, fibrosing alveolitis, and acute respiratory distress syndrome;

malignancies, such as colorectal cancer, and malignant melanoma;

transplantation-derived disorders, such as allograft and xenograft rejection, and graft-versus-host disease;

endocrinologic disorders, such as autoimmune thyroiditis and Grave's disease;

vascular disorders, such as Wegener's granulomatosis, microscopic polyangiitis, polyarteritis nodosa, giant-cell arteritis, and atherosclerosis;

gynecological-obstetrical disorders, such as recurrent spontaneous abortion, and endometriosis; and infectious diseases, such as sepsis, and AIDS.

In yet a further embodiment, the disorder is selected from the group consisting of ankylosing spondylitis, systemic lupus erythematosus, ulcerative colitis, allograft rejection and graft-versus-host disease.

The human antibodies of the present invention may also be combined with one or more additional therapeutic agents, such as anti-inflammatory agents, DMARDs (disease-modifying anti-rheumatic drugs), immunosuppressive agents, chemotherapeutics, and psoriasis agents.

In one embodiment, the subject can be additionally treated with one or more agents that enhance the inhibition of the proinflammatory effect of the antibodies, e.g., an anti-inflammatory agent, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, the human antibodies of the invention can be administered in combination with one or more DMARDs, such as methotrexate (Rheumatrex), hydroxychloroquine (Plaquenil), sulfasalazine (Asulfidine), pyrimidine synthesis inhibitors, e.g. leflunomide (Arava), IL-1 receptor blocking agents, e.g. anakinra (Kineret), and TNF-α blocking agents, e.g. etanercept (Enbrel), infliximab (Remicade) and adalimumab.

Further examples are IL-10, soluble IL-15R, anti-IL6R antibodies, CTLA4Ig, and anti-CD20 antibodies.

In another embodiment, the human antibodies of the invention can be administered in combination with one or more immunosuppressive agents, such as cyclosporine (Sandimmune, Neoral) and azathioprine (Imural).

Further examples are mycophenolic acid, mycophenolate mofetil, corticosteroids, such as prednisone, methotrexate, gold salts, sulfasalazine, antimalarials, brequinar, leflunomide, mizoribine, 15-deoxyspergualine, 6-mercapto-purine, cyclophosphamide, rapamycin, tacrolimus (FK-506), and anti-thymocyte globulin.

In another embodiment, the human antibodies of the invention can be administered in combination with two or more immunosuppressive agents, such as prednisone and cyclosporine; prednisone, cyclosporine and azathioprine; or prednisone, cyclosporine and mycophenolate mofetil.

In another embodiment, the human antibodies of the invention can be administered in combination with one or more chemotherapeutics, such as doxorubicin (Adriamycin), cisplatin (Platinol), bleomycin (Blenoxane), carmustine (Gliadel), cyclophosphamide (Cytoxan, Procytox, Neosar), and chlorambucil (Leukeran). The human antibodies according to the invention can also be administered in conjunction with radiation therapy.

In another embodiment, the human antibodies of the invention can be administered in combination with one or more agents for treating psoriasis, such as topical medications containing coal tar, A vitamin, cortisone or other corticosteroids, oral or injected medications, such as corticosteroids, methotrexate, retinoids, e.g. acicretin (Neogitason) or cyclosporine (Sandimmune, Neoral). Other treatments may include exposure to sunlight or phototherapy.

Further examples are anthralin, calcipotrien, tarazotene, etanercept, alefacept, efalizumab, 6-thioguanine, mycophenolate mofetil, tacrolimus (FK-506), and hydroxyurea. Other examples are CTLA4Ig and infliximab. Other treatments may include UVB (broad-band and narrow-band ultraviolet B), UVA (ultraviolet A) and PUVA (psoralen methoxalen plus ultraviolet A).

In a further embodiment, the compositions of the invention are administered in conjunction with two or more of the above therapies, such as methotrexate+phototherapy (PUVA or UVA); methotrexate+acitretin; acitretin+phototherapy (PUVA or UVA); methotrexate+acitretin+phototherapy (PUVA or UVB; hydroxyurea+phototherapy (PUVA or UVB); hydroxyurea+acitretin; cyclosporine+methotrexate; or calcipotrien+phototherapy (UVB).

In another embodiment, the human antibodies of the invention can be administered in combination with other antibodies, such as CD4 specific antibodies and IL-2 specific antibodies. A combination of the present human antibodies with CD4 specific antibodies or IL-2 specific antibodies are considered particularly useful for treating autoimmune diseases and transplant rejections.

In still another embodiment, the present antibodies may be administered in combination with other antibodies, e.g. other immunosuppressive human monoclonal antibodies, such as antibodies binding to, e.g., MHC, CD2, CD3, CD7, CD28, B7, CD40, CD45, IFN-γ, TNF-α, IL-2R, IL-4, IL-5, IL-6R, IL-7, IL-8, IL-10, CD11a, CD20 or CD58, or their ligands; or other immunomodulatory compounds, e.g., soluble IL-15R or IL-10.

In yet another aspect, the present invention provides a method for detecting in vitro or in vivo the presence of the IL-15 antigen in a sample, e.g., to diagnose IL-15-mediated diseases. In one embodiment, this is achieved by contacting a sample to be tested, along with a control sample, with a human monoclonal antibody of the invention, or an antigen-binding portion thereof under conditions that allow for formation of a complex between the antibody and IL-15. Complex formation is then detected (e.g., using an ELISA) in both samples, and any statistically significant difference in the formation of complexes between the samples is indicative of the presence of the IL-15 antigen in the test sample.

Other features and advantages of the instant invention will be apparent from the following detailed description and claims.

BRIEF DESCRIPTION OF THE DRAWINGS

FIGS. 2 and 3 show amino acid (SEQ ID NOs:2 and 4) and nucleotide (SEQ ID NOs:1 and 3) sequences of the $V_H$ and $V_L$-regions, respectively, from antibody 146B7. The framework (FR) and complementarity determining regions (CDR) are indicated.

FIGS. 7-9 include graphs showing the inhibitory activity of antibodies 146B7 (FIG. 7), 404E4 (FIG. 8) and 404A8 (FIG. 9) on IL-15 induced PBMC proliferation. Human PBMC were incubated with hIL-15 (0, 25, 100 ng/ml.

FIG. 14 includes graphs showing the effects of antibody 146B7 treatment in SCID/psoriasis mice. Biopsies were fixed in formalin for paraffin embedding and stained in H&E and for Ki-67 nuclear antigen.

FIG. 15 shows H&E staining of human psoriatic skin engrafted in SCID mice, after treatment with antibody 146B7 (panel C), with CsA (panel B), or with vehicle (panel A). Three weeks after transplantation mice received PBS (placebo), CsA (cyclosporine A) (Sandoz) at a dose of 10 mg/kg every second day for 15 days, or 146B7 at a dose of 20 mg/kg on day 1 and 10 mg/kg on days 8 and 15. One week after the last injection, mice were sacrificed, and a 4 mm punch biopsy was taken from each xenograft. Biopsies were fixed in formalin for paraffin embedding and stained in H&E.

FIG. 16 shows Ki-67 staining of human psoriatic skin engrafted in SCID mice, after treatment with 146B7 (panel C), with CsA (panel B), or with vehicle (panel A). Three weeks after transplantation mice received PBS (placebo), CsA (cyclosporine A) (Sandoz) at a dose of 10 mg/kg every second day for 15 days, or 146B7 at a dose of 20 mg/kg on day 1 and 10 mg/kg on days 8 and 15. One week after the last injection, mice were sacrificed, and a 4 mm punch biopsy was taken from each xenograft. Biopsies were fixed in formalin for paraffin embedding and stained for Ki-67 nuclear antigen.

DETAILED DESCRIPTION OF THE INVENTION

Figure 1:
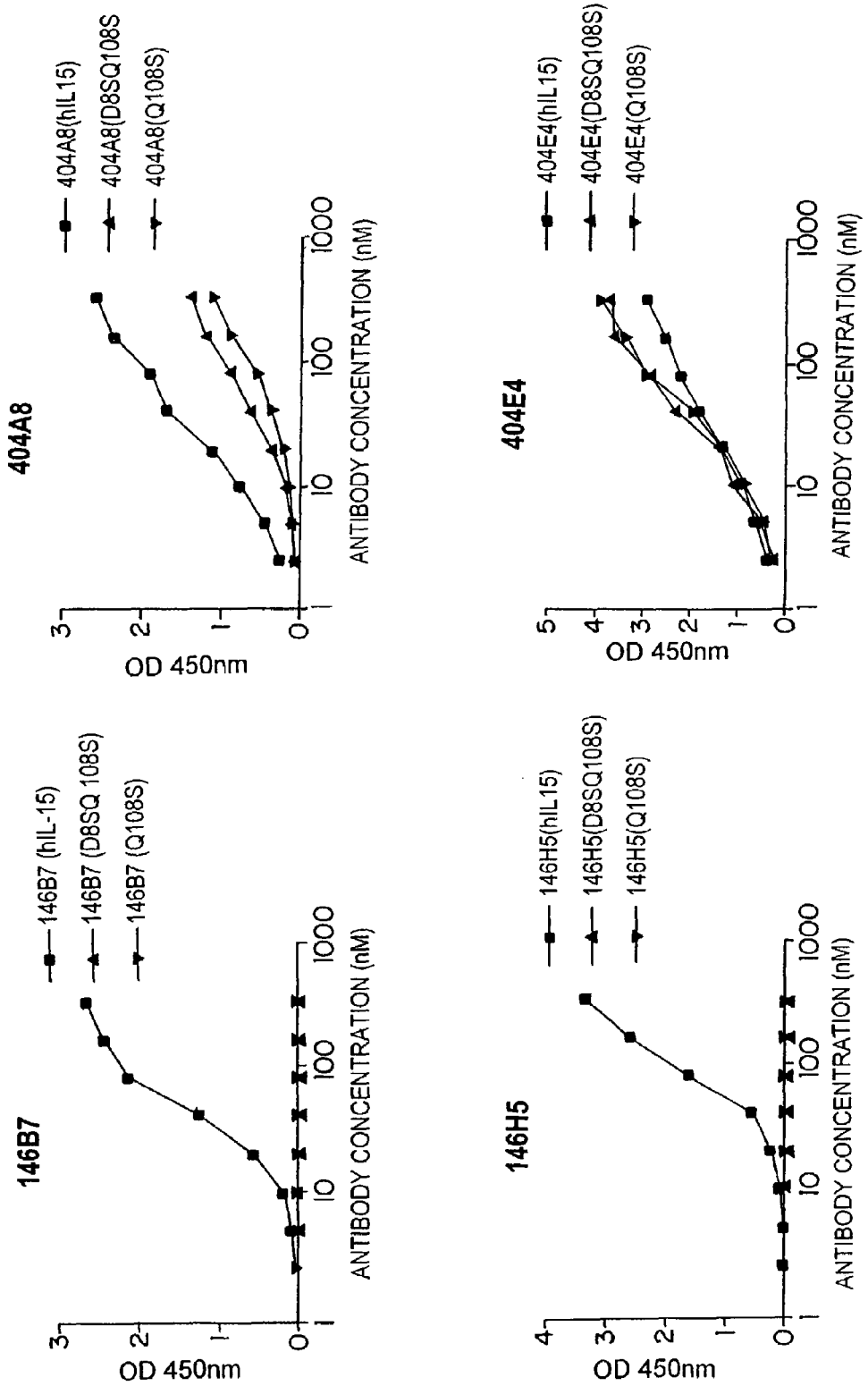
FIG. 1 includes graphs showing the binding of the human IL-15 specific antibodies, 146B7, 147H5, 404A8 and 404E4, to human IL-15 (hIL-15) and to the mutant IL-15 proteins, Q108S and D8SQ108S. Serial dilutions of the antibodies were examined for their binding to hIL-15 or the mutant IL-15 proteins D8SQ108S and Q108S in an ELISA.

The present invention provides novel antibody-based therapeutics for treating and diagnosing a variety of disorders mediated by IL-15 (i.e., disorders caused by the proinflammatory effects of IL-15). As used herein, the term "proinflammatory effects of IL-15" includes any humoral or cell-mediated immune response induced by IL-15, such as production of TNFα and other inflammatory mediators, and recruitment/proliferation of T-cells. Therapies of the invention employ isolated human monoclonal antibodies which specifically bind to an epitope present on IL-15.

In one embodiment, the human antibodies are produced in a non-human transgenic animal, e.g., a transgenic mouse, capable of producing multiple isotypes of human monoclonal antibodies to IL-15 (e.g., IgG, IgA and/or IgE) by undergoing V-D-J recombination and isotype switching. Accordingly, various aspects of the invention include antibodies and pharmaceutical compositions thereof, as well as non-human transgenic animals, B-cells, host cell transfectomas, and hybridomas for making such monoclonal antibodies. Methods of using the antibodies of the invention to detect cells to which IL-15 is bound, and/or to inhibit IL-15 mediated functions either in vitro or in vivo, are also encompassed by the invention. Methods for targeting agents to cells to which IL-15 is bound are also included.

In order that the present invention may be more readily understood, certain terms are first defined. Additional definitions are set forth throughout the detailed description.

The terms "IL-15," "IL-15 antigen" and "Interleukin 15" are used interchangeably herein, and include any variants or isoforms which are naturally expressed by cells.

The term "antibody" as referred to herein includes whole antibodies and any antigen binding fragment (i.e., "antigen-binding portion") or single chain thereof. An "antibody"

refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $CH_1$, $CH_2$ and $CH_3$. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IL-15). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody", as used herein, is intended to refer to an antibody which is substantially free of other antibodies having different antigenic specificities (e.g., an isolated antibody that specifically binds to IL-15 is substantially free of antibodies that specifically bind antigens other than IL-15). An isolated antibody that specifically binds to an epitope of IL-15 may, however, have cross-reactivity to other related cytokines or to other IL-15 proteins from different species. However, the antibody preferably always binds to human IL-15. In addition, an isolated antibody is typically substantially free of other cellular material and/or chemicals. In one embodiment of the invention, a combination of "isolated" monoclonal antibodies having different IL-15 specificities are combined in a well defined composition.

As used herein, "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant human IL-15 as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$K_D$", as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., $V_H$, $V_L$, CDR3) that bind to IL-15, is intended to refer to a nucleic acid molecule in which the nucleotide sequences encoding the antibody or antibody portion are free of other nucleotide sequences encoding antibodies or antibody portions that bind antigens other than IL-15, which other sequences may naturally flank the nucleic acid in human genomic DNA. SEQ ID NOS: 1-4 correspond to the nucleotide and amino acid sequences comprising the heavy chain ($V_H$) and light chain ($V_L$) variable regions of the human anti-IL-15 antibody 146B7 of the invention. In particular, SEQ ID NO:1 and 2 correspond to the $V_H$ of the 146B7 antibody, SEQ ID NO:3 and 4 correspond to the $V_L$ of the 146B7 antibody.

The present invention also encompasses "conservative sequence modifications" of the sequences set forth in SEQ ID NOs: 1-4, i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs:1-4 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IL-15 antibody is preferably replaced with another amino acid residue from the same side chain family.

Alternatively, in another embodiment, mutations can be introduced randomly along all or part of a anti-IL-15 antibody coding sequence, such as by saturation mutagenesis, and the resulting modified anti-IL-15 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-4) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID Nos:1-4 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For amino acid sequences, the term "homology" indicates the degree of identity between two amino acid sequences when optimally aligned and compared with appropriate insertions or deletions.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "subject" includes any human or non-human animal. For example, the methods and compositions of the present invention can be used to treat a subject with an inflammatory disease, such as arthritis, e.g., rheumatoid arthritis. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

I. Production of Human Antibodies to IL-15

Human monoclonal antibodies of the invention can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for generating hybridomas which produce human monoclonal antibodies of the invention is the murine system. Hybridoma production in the mouse is well known in the art, including immunization protocols and techniques for isolating and fusing immunized splenocytes.

In one embodiment, human monoclonal antibodies directed against IL-15 are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol. Vol.* 13: 65-93, and Harding, F. and Lonberg, N. (1995) Ann. N.Y. Acad. Sci. 764:536-546). The preparation of HuMAb mice is described in detail in Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13: 65-93; Harding, F. and Lonberg, N. (1995) *Ann. N.Y. Acad. Sci.* 764:536-546; Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992. The preparation of HCO12 transgenic HuMAb mice, in particular, is described in Example 2.

Immunizations

To generate fully human monoclonal antibodies to IL-15, transgenic or transchromosomal mice containing human immunoglobulin genes (e.g., HCo12, HCo7 or KM mice) can be immunized with a purified or enriched preparation of the IL-15 antigen and/or cells expressing IL-15, as described, for example, by Lonberg et al. (1994) *Nature* 368(6474): 856-859; Fishwild et al. (1996) *Nature Biotechnology* 14: 845-851 and WO 98/24884. Alternatively, mice can be immunized with DNA encoding human IL-15. Preferably, the mice will be 6-16 weeks of age upon the first infusion. For example, a purified or enriched preparation (5-50 μg) of the IL-15 antigen can be used to immunize the HuMAb mice intraperitoneally. In the event that immunizations using a purified or enriched preparation of the IL-15 antigen do not result in antibodies, mice can also be immunized with cells expressing IL-15, e.g., a cell line, to promote immune responses.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital bleeds. The plasma can be screened by ELISA (as described below), and mice with sufficient titers of anti-IL-15 human immunoglobulin can be used for fusions. Mice can be boosted intravenously with antigen 3 days before sacrifice and removal of the spleen.

Generation of Hybridomas Producing Human Monoclonal Antibodies to IL-15

To generate hybridomas producing human monoclonal antibodies to IL-15, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human anti-IL-15 monoclonal IgM and IgG antibodies. Once extensive hybridoma growth occurs, medium can be observed usually after 10-14 days. The antibody secreting hybridomas can be replated, screened again, and if still positive for human IgG, anti-IL-15 monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to IL-15

Human antibodies of the invention also can be produced in a host cell transfectoma using, for example, a combination of recombinant DNA techniques and gene transfection methods as is well known in the art (Morrison, S. (1985) *Science* 229:1202).

For example, in one embodiment, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fingi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as *E. coli* or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGK are described below (Example 1). The plasmids were constructed so that PCR amplified V heavy and V kappa light chain cDNA sequences could be used to reconstruct complete heavy and light chain minigenes. These plasmids can be used to express completely human $IgG_1\kappa$ or $IgG_4\kappa$ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, the structural features of an human anti-IL-15 antibodies of the invention, 146B7, 147H5, 404A8 and 404E4, are used to create structurally related human anti-IL-15 antibodies that retain at least one functional property of the antibodies of the invention, such as binding to IL-15. More specifically, one or more CDR regions of 146B7, 147H5, 404A8 and 404E4 can be combined recombinantly with known human framework regions and CDRs to create additional, recombinantly-engineered, human anti-IL-15 antibodies of the invention.

Figure 2:
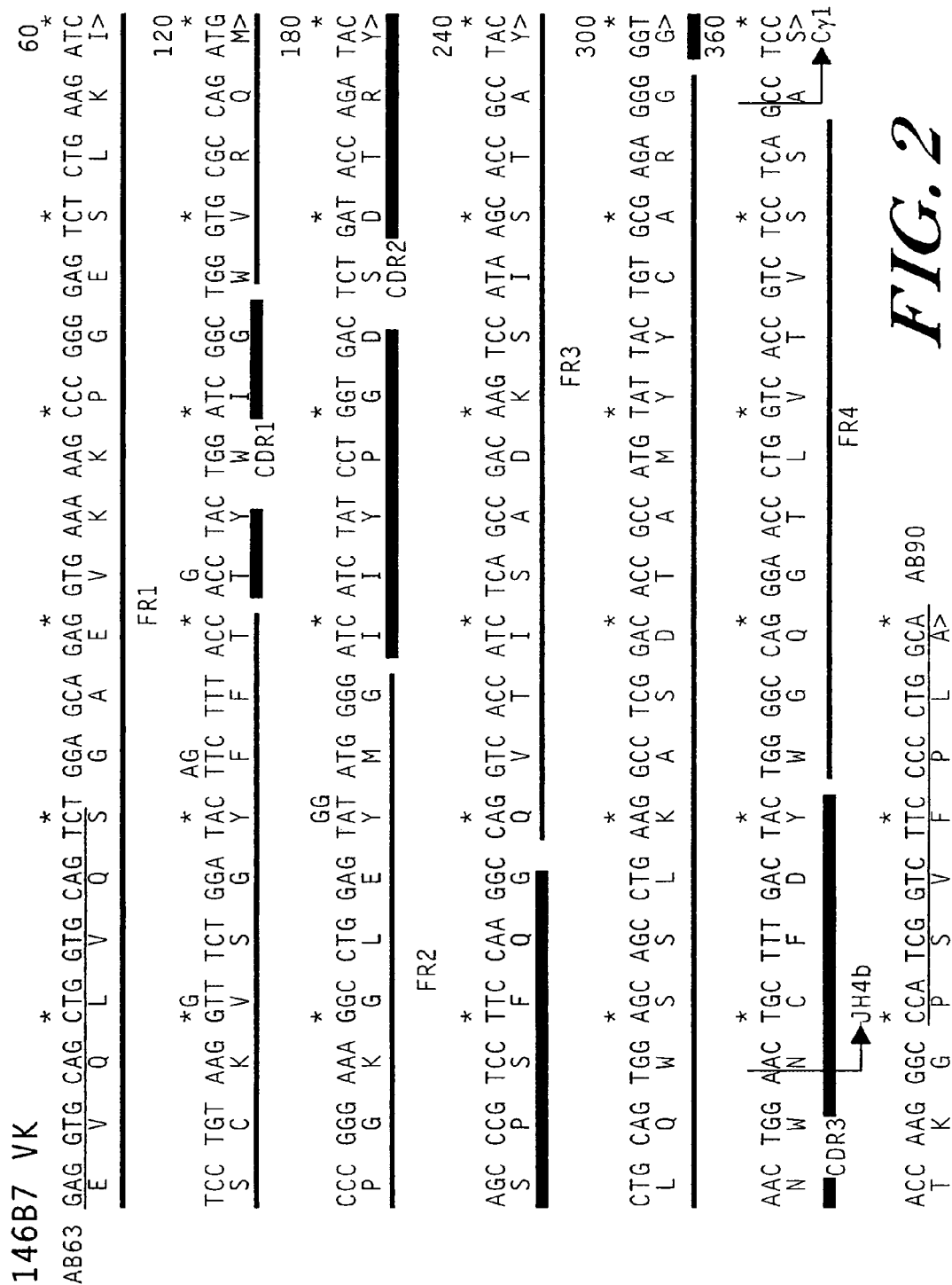
Figure 4A:
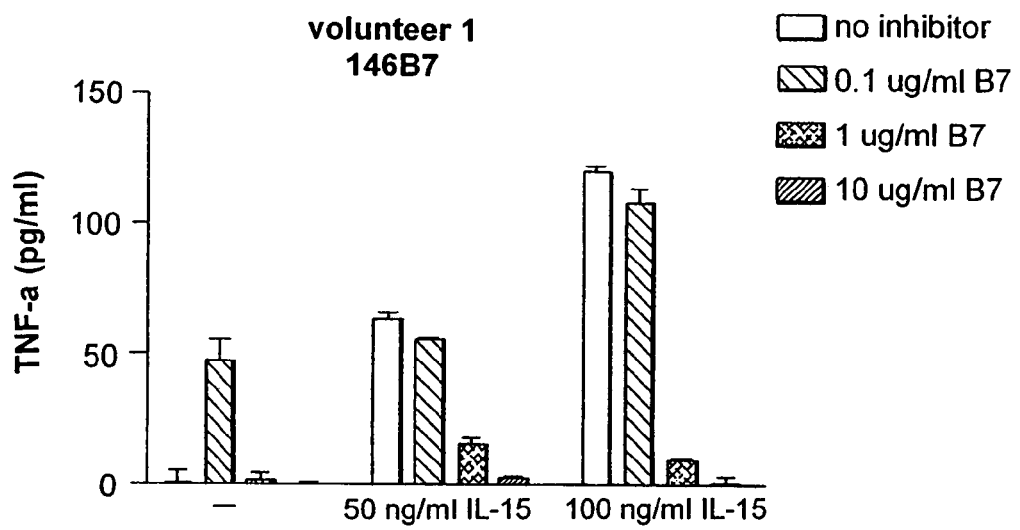
FIGS. 4A-D include graphs showing the inhibition of IL-15-mediated TNF-α release by antibody 146B7. Human PBMC were incubated with hIL-15 (0, 50, 100 ng/ml) in combination with 146B7 antibody or with an isotype control antibody (0.1, 1, 10 µg/ml) for 72 hours. The amount of TNF-α produced was measured by ELISA. Data from two healthy volunteers are shown.
Figure 4B:
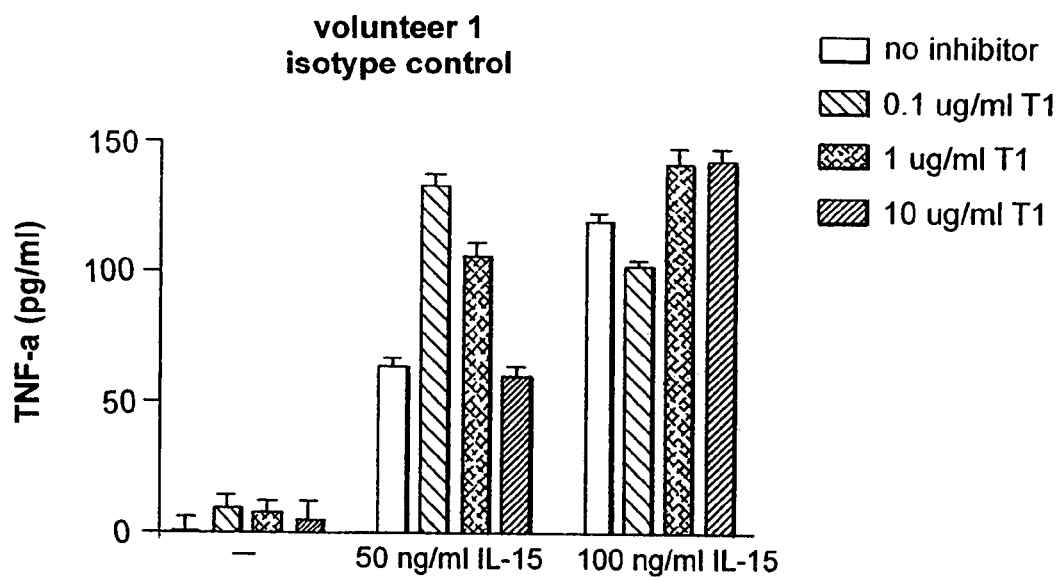
Figure 4C:
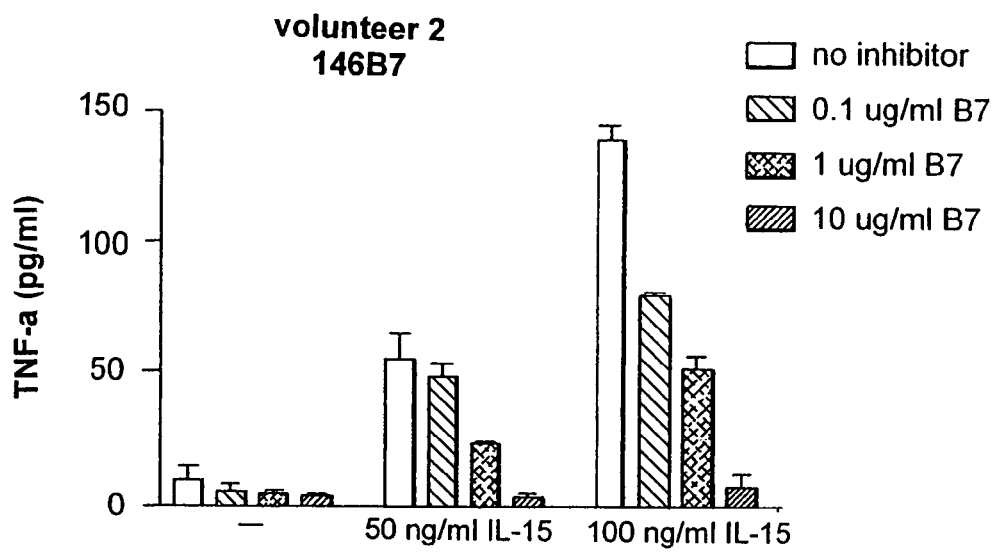
Figure 4D:
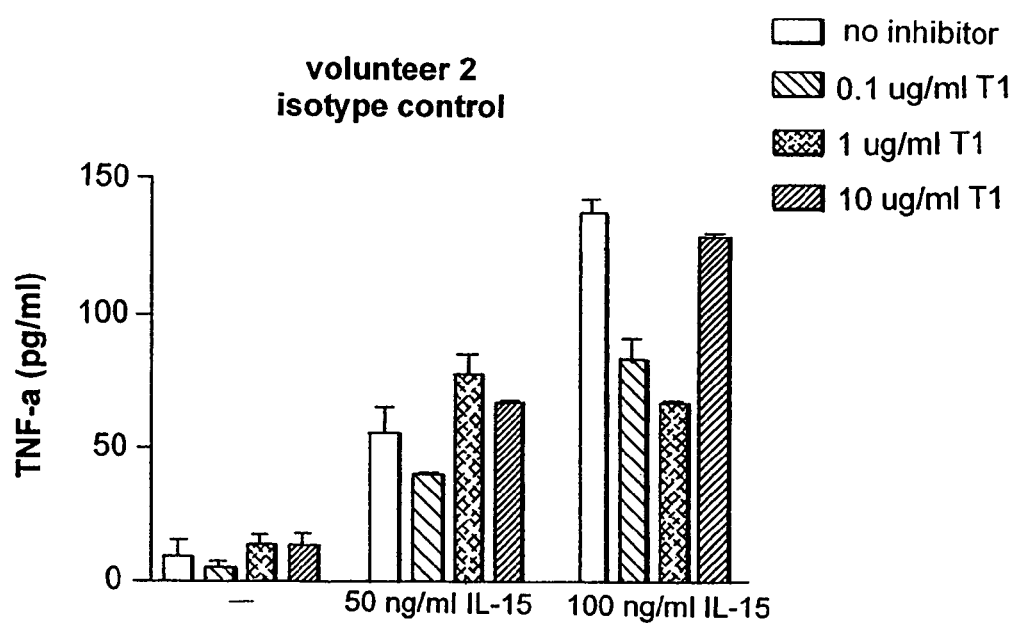

Accordingly, in another embodiment, the invention provides a method for preparing an anti-IL-15 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIG. 2 (or corresponding amino acid residues in SEQ ID NO: 2); and (2) human light chain framework regions and human light chain CDRs, wherein at least one of the human heavy chain CDRs comprises an amino acid sequence selected from the amino acid sequences of CDRs shown in FIG. 3 (or corresponding amino acid residues in SEQ ID NO: 4);

wherein the antibody retains the ability to bind to IL-15. The ability of the antibody to bind IL-15 can be determined using standard binding assays, such as those set forth in the Examples (e.g., an ELISA).

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of 146B7, 147H5, 404A8 and 404E4. The antibodies further can comprise the CDR2s of 146B7, 147H5, 404A8 and 404E4. The antibodies further can comprise the CDR1s 146B7, 147H5, 404A8 and 404E4. The antibodies can further comprise any combinations of the CDRs.

Accordingly, in another embodiment, the invention further provides anti-IL-15 antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of 146B7, 147H5, 404A8 and 404E4, for example, a human heavy chain CDR region of 146B7 as shown in FIG. 2 (or corresponding amino acid residues in SEQ ID NO: 2); and (2) human light chain framework regions, a human light chain CDR1 region, a human light chain CDR2 region, and a human light chain CDR3 region, wherein the human light chain CDR3 region is selected from the CDR3s of 146B7, 147H5, 404A8 and 404E4, for example, a human light chain CDR region of 146B7 as shown in FIG. 3 (or corresponding amino acid residues in SEQ ID NO: 4), wherein the antibody binds IL-15. The antibody may further comprise the heavy chain CDR2 and/or the light chain CDR2 of 146B7, 147H5, 404A8 and 404E4. The antibody may further comprise the heavy chain CDR1 and/or the light chain CDR1 of 146B7, 147H5, 404A8 and 404E4.

The CDR 1, 2, and/or 3 regions of the engineered antibodies described above can comprise the exact amino acid sequence(s) as those of 146B7, 147H5, 404A8 and 404E4 disclosed herein. However, the ordinarily skilled artisan will appreciate that some deviation from the exact CDR sequences of 146B7, 147H5, 404A8 and 404E4 may be possible while still retaining the ability of the antibody to bind IL-15 effectively (e.g., conservative sequence modifications). Accordingly, in another embodiment, the engineered antibody may be composed of one or more CDRs that are, for example, 90%, 95%, 98% or 99.5% identical to one or more CDRs of 146B7, 147H5, 404A8 and 404E4.

In addition to simply binding IL-15, engineered antibodies such as those described above may be selected for their retention of other functional properties of antibodies of the invention, such as:

(1) binding to human IL-15 and inhibiting IL-15 induced proinflammatory effects;

(2) inhibiting IL-15 induced TNFα production or T cell proliferation;

(3) binding to human IL-15 with a dissociation equilibrium constant ($K_D$) of less than approximately $10^{-7}$ M when determined by surface plasmon resonance (SPR) technology in a BIACORE 3000 instrument using recombinant human IL-15 as the analyte and the antibody as the ligand;

(4) binding to an epitope located on the β— and/or γ-chain interacting domain of human IL-15;

(5) interfering with the binding of $Asp^8$ of human IL-15 to the β-unit of the human IL-15 receptor and/or of $Gln^{108}$ of human IL-15 to the γ-unit of human IL-15 receptor;

(6) binding to receptor-bound human IL-15;

(7) binding to human IL-15 and inhibiting the ability of human IL-15 to induce parakeratosis;

(8) binding to human IL-15 and inhibiting the ability of human IL-15 to induce epidermal thickening;

(9) binding to human IL-15 and inhibiting the ability of human IL-15 to induce proliferation of keratinocytes; and/or

(10) binding to human IL-15 and inhibiting the ability of human IL-15 to induce chemotaxis of activated leukocytes.

Characterization of Human Monoclonal Antibodies to IL-15

Human monoclonal antibodies of the invention can be characterized for binding to IL-15 using a variety of known techniques. Generally, the antibodies are initially characterized by ELISA. Briefly, microtiter plates can be coated with purified IL-15 in PBS, and then blocked with irrelevant proteins such as bovine serum albumin (BSA) diluted in PBS. Dilutions of plasma from IL-15-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the IL-15 immunogen. Hybridomas that bind, preferably with high affinity, to IL-15 can than be subcloned and further characterized. One clone from each hybridoma, which retains the reactivity of the parent cells (by ELISA), can then be chosen for making a cell bank, and for antibody purification.

To purify human anti-IL-15 antibodies, selected hybridomas can be grown in roller bottles, two-liter spinner-flasks or other culture systems. Supernatants can be filtered and concentrated before affinity chromatography with protein A-sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected human anti-IL-15 monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-human Ig overnight at 4° C. After blocking with 5% BSA, the plates are reacted with 10 µg/ml of monoclonal antibodies or purified isotype controls, at ambient temperature for two hours. The wells can then be reacted with either human IgG1 or other human isotype specific conjugated probes. Plates are developed and analyzed as described above.

To test the binding of monoclonal antibodies to live cells expressing IL-15, flow cytometry can be used. Briefly, cell lines and/or human PBMCs expressing membrane-bound IL-15 (grown under standard growth conditions) are mixed with various concentrations of monoclonal antibodies in PBS containing 0.1% BSA and 0.01% NaN3 at 4° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-IL-15 human IgGs can be further tested for reactivity with the IL-15 antigen by Western blotting. Briefly, cell extracts from cells expressing IL-15 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

II. Production of Transgenic and Transchromosomal Nonhuman Animals which Generate Human Monoclonal Anti-IL-15 Antibodies In yet another aspect, the invention provides transgenic and transchromosomal non-human animals, such as transgenic or transchromosomal mice, which are capable of expressing human monoclonal antibodies that specifically bind to IL-15. In a particular embodiment, the invention provides a transgenic or transchromosomal mouse having a genome comprising a human heavy chain transgene, such that the mouse produces human anti-IL-15 antibodies when immunized with IL-15 antigen and/or cells expressing IL-15. The human heavy chain transgene can be integrated into the chromosomal DNA of the mouse, as is the case for transgenic, e.g., HuMAb mice, as described in detail herein and exemplified. Alternatively, the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to IL-15 (e.g., IgG, IgA and/or IgE) by undergoing V-D-J recombination and isotype switching. Isotype switching may occur by, e.g., classical or non-classical isotype switching.

The design of a transgenic or transchromosomal non-human animal that responds to foreign antigen stimulation with a heterologous antibody repertoire, requires that the heterologous immunoglobulin transgenes contained within the transgenic animal function correctly throughout the pathway of B-cell development. This includes, for example, isotype switching of the heterologous heavy chain transgene. Accordingly, transgenes are constructed so as to produce isotype switching and one or more of the following of antibodies: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y.

In certain embodiments, the transgenic or transchromosomal non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to the IL-15 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic or transchromosomal animal used to generate human antibodies to IL-15 contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

Transgenic and transchromosomal mice employed in the present invention exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a native mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity ($K_D$) for preselected antigens of below $10^{-7}$ M, such as of below $10^{-8}$ M, $10^{-9}$ M or $10^{-10}$ M or even lower.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g. by hybridization or DNA sequencing, as being from a species of organism other than the transgenic animal.

Transgenic and transchromosomal mice as described above can be immunized with, for example, a purified or enriched preparation of IL-15 antigen and/or cells expressing IL-15. Alternatively, the transgenic mice can be immunized with DNA encoding human IL-15. The mice will then produce B cells which undergo class-switching via intratransgene switch recombination (cis-switching) and express immunoglobulins reactive with IL-15. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ or $V_H$ gene segment and a human $J_L$ or $D_H$ and $J_H$ segment, even though other non-germline sequences may be present as a result of somatic mutation and differential V-J and V-D-J recombination joints. The variable regions of each antibody chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Human antibodies which bind to the predetermined antigen can result from isotype switching, such that human antibodies comprising a human sequence γ chain (such as γ1, γ2a, γ2B, or γ73) and a human sequence light chain (such as kappa) are produced. Such isotype-switched human antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human antibodies may have binding affinities ($K_D$) of below $10^{-7}$ M, such as of below $10^{-8}$ M, $10^{-9}$ M or $10^{-10}$ M or even lower.

Another aspect of the invention includes B cells derived from transgenic or transchromosomal mice as described herein. The B cells can be used to generate hybridomas expressing human monoclonal antibodies which bind with high affinity (e.g., lower than $10^{-7}$ M) to human IL-15. Thus, in another embodiment, the invention provides a hybridoma which produces a human antibody having an affinity ($K_D$) of below $10^{-7}$ M, such as of below $10^{-8}$ M, $10^{-9}$ M or $10^{-10}$ M or even lower when determined by surface plasmon resonance (SPR) technology in a BIACORE 3000 instrument using recombinant human IL-15 as the analyte and the antibody as the ligand for binding human IL-15, wherein the antibody comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human CL gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against IL-15 can be facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animal containing rearranged heavy and an unrearranged light immunoglobulin transgene; and IV. Transgenic animals containing rearranged heavy and rearranged light immunoglobulin transgenes.

Of these categories of transgenic animal, the preferred order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Antibody Conjugates/Immunotoxins

In another aspect, the present invention features a human anti-IL-15 monoclonal antibody conjugated to a therapeutic moiety, such as a cytotoxin, a drug (e.g., an immunosuppressant) or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a IL-15-related disorder, such as a cancer.

The antibody conjugates of the invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

IV. Pharmaceutical Compositions

In another aspect, the present invention provides a composition, e.g., a pharmaceutical composition, containing one or a combination of human monoclonal antibodies, or antigen-binding portion(s) thereof, of the present invention, formulated together with a pharmaceutically acceptable carrier. In a preferred embodiment, the compositions include a combination of multiple (e.g., two or more) isolated human antibodies of the invention. Preferably, each of the antibodies of the composition binds to a distinct, pre-selected epitope of IL-15.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, chemotherapeutics, and psoriasis agents. The pharmaceutical compositions of the invention can also be administered in conjunction with radiation therapy. Co-administration with other antibodies, such as CD4 specific antibodies and IL-2 specific antibodies, are also encompassed by the invention. Such combinations with CD4 specific antibodies or IL-2 specific antibodies are considered particularly useful for treating autoimmune diseases and transplant rejections.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In a further embodiment, the human monoclonal antibodies of the invention can be formulated to prevent or reduce the transport across the placenta. This can be done by methods known in the art, e.g., by PEGylation of the antibody or by use of F(ab)2' fragments. Further references can be made to "Cunningham-Rundles C, Zhuo Z, Griffith B, Keenan J. (1992) Biological activities of polyethylene-glycol immunoglobulin conjugates. Resistance to enzymatic degradation. J Immunol Methods. 152:177-190; and to "Landor M. (1995) Maternal-fetal transfer of immunoglobulins, Ann Allergy Asthma Immunol 74:279-283. This is particularly relevant when the antibodies are used for treating or preventing recurrent spontaneous abortion.

A "therapeutically effective dosage" for rheumatoid arthritis preferably will result in an ACR20 Preliminary Definition of Improvement in the patients, more preferred in an ACR50 Preliminary Definition of Improvement and even more preferred in an ARCD70 Preliminary Definition of Improvement.

ACR20 Preliminary Definition of Improvement is defined as:

$\geq$20% improvement in: Tender Joint Count (TCJ) and Swollen Joint Count (SWJ) and $\geq$20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR).

ACR50 and ACR70 are defined in the same way with $\geq$50% and $\geq$70% improvements, respectively. For further details see Felson et al. in American College of Rheumatology Preliminary Definition of Improvement in Rheumatoid Arthritis; Arthritis Rheumatism (1995) 38: 727-735.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The ability of the antibodies to treat or prevent psoriasis can also be evaluated according to methods well known in the art.

The composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

V. Uses and Methods of the Invention

Human anti-IL-15 antibodies to IL-15 of the present invention (including derivatives and conjugates of the antibodies) and compositions containing the antibodies can be used in a variety of in vitro and in vivo diagnostic and therapeutic applications.

In one embodiment, human antibodies of the invention are used to inhibit IL-15 induced TNFα production by T cells and/or monocytes/macrophages, preferably without inhibiting TNFα production induced by other cytokines, such as IL-2. By contacting the antibody with IL-15 (e.g., by administering the antibody to a subject), the ability of IL-15 to signal through the IL-15 receptor is inhibited and, thus, the production of TNFα by T-cells and/or monocytes/macrophages also is inhibited. Preferred antibodies bind to epitopes (e.g., particular subunits, such as the gamma subunit) which are specific to IL-15 and, thus, advantageously inhibit IL-15-induced TNFα production, but do not interfere with TNFα production by structurally related cytokines, such as IL-2.

Alternatively, human antibodies are used to interfere with IL-15 receptor α-, β- and γ-chain assembly and/or inhibit assembly on neighbouring cells expressing β- and γ-chains as part of the IL-15 receptor or another cytokine receptor.

In another embodiment, human antibodies of the invention are used to inhibit IL-15 induced T cell recruitment and/or proliferation, preferably without inhibiting T cell proliferation induced by other structurally related cytokines, such as IL-2. As with TNFα production, by contacting the antibody with IL-15 (e.g., by administering the antibody to a subject), the ability of IL-15 to signal through the IL-15 receptor is inhibited and, thus, T cell stimulation by IL-15 is inhibited.

Accordingly, in yet another embodiment, the present invention provides a method for treating or preventing a disorder mediated by IL-15 (e.g., an autoimmune disease, such as psoriasis, rheumatoid arthritis, or inflammatory bowel disease, or an infectious disease, such as HIV), by administering to a subject a human antibody of the invention in an amount effective to treat or prevent the disorder. The antibody can be administered alone or along with another therapeutic agent, such as an anti-inflammatory agent, e.g., a steroidal or non-steroidal inflammatory agent, or a cytotoxin which acts in conjunction with or synergistically with the antibody to treat or prevent the IL-15 mediated disease.

In a particular embodiment, human antibodies of the present invention are used to treat or to prevent rheumatoid arthritis (RA). The antibodies limit the role that IL-15 plays in the progression of inflammation associated with diseases such as RA. T cells, particularly CD4+ T-helper cells, are involved in the initiation and maintenance of inflammatory processes in RA. TNF-α, another cytokine, is also involved in the inflammatory pathways which ultimately lead to joint destruction and incapacitation of the patient with RA. Local synthesis of IL-15 plays a key role both in the activation and recruitment of T cells and in the induction of TNF-α and other inflammatory cytokines. The role of IL-15 in the progression of RA involves a process whereby IL-15, which is synthesized by macrophages, induces T cell recruitment. The activated T cells then: (1) maintain macrophage activation; and (2) induce TNF-α production. Stimulated macrophages promote the synthesis of more IL-15 and T cell activation, thus, continuing the cycle. In addition to its effects on TNF-α and macrophages, IL-15 also activates neutrophils and affects local B cell immunoglobulin secretion, particularly rheumatoid factor synthesis.

Accordingly, anti-IL-15 antibodies of the invention can be used to prevent or block the foregoing effects of IL-15 which cause RA and, thus, can be used to prevent or treat this disease. For example, anti-IL-15 antibodies of the invention can be used to inhibit inflammation and/or prevent chemotaxis of activated leukocytes involved in RA.

The human antibodies of the present invention may be used for inhibition of progression of structural damage in patients with rheumatoid arthritis who have had an inadequate response to methotrexate or for reducing sign and symptoms and delaying structural damage in patients with moderately to severely active rheumatoid arthritis, including those who have not previously failed treatment with a DMARD.

Human antibodies of the present invention also can be used to block or inhibit other effects of IL-15. IL-15 is expressed in various cells and tissues including monocytes and macrophages, fibroblasts, dendritic cells, and keratinocytes. Keratinocytes are major constituents of the epidermis and the epithelial lining of mucosal tissue. Control of keratinocyte growth is mediated by a complex network of cytokines and growth factors, some of which are produced by keratinocytes themselves. Keratinocyte-derived IL-15 contributes to T cell accumulation, proliferation, and survival in psoriatic plaques. Many diseases are known wherein the number of keratinocytes is increased which leads to epidermal hyperplasia which is responsible for at least some of the related disease symptoms. These diseases include chronic diseases such as psoriasis and atopic dermatitis, as well as conditions like chronic hand eczema, contact dermatitis, viral warts (HPV associated), cutaneous T cell lymphoma, impaired wound healing, such as impaired wound healing due to diabetes. Accordingly, the invention provides methods for treating or preventing such disorders by administering to patients a human anti-IL-15 antibody of the invention in an amount effective to treat or prevent the disorder. For example, anti-IL-15 antibodies of the invention can be used to block or inhibit parakeratosis in psoriasis, reduce epidermal thickness in psoriasis, and reduce proliferation of keratinocytes in psoriasis.

IL-15 also modulates the function of intestinal epithelial cells (Reinecker, et al. (1996) Gastroenterology 111:1706-13). Specifically, IL-15 can cause modifications on mucosal epithelial cells and on intestinal epithelial cell lines and, therefore, is involved in the pathogenesis of inflammatory bowel disease, e.g., celiac disease. The role of IL-15 in such diseases is shown by the selective over-representation of IL-15+ cells in the small intestine of untreated patients with celiac disease (WO 00/02582). Thus, it has been shown that IL-15 is directly involved in the initiation and maintenance of celiac disease. Accordingly, in another embodiment, anti-IL-15 human antibodies of the present invention (i.e., which inhibit the proinflammatory effects of IL-15) can be used to treat and/or to prevent celiac disease by administering the antibody to a patient in an amount effective to treat or prevent the disorder.

In addition, it has been found by the inventors of the present invention that IL-15 also promotes the formation of new blood vessels, a process called neovascularization or angiogenesis. Accordingly, yet another use for the antibodies of the invention includes the prevention or treatment of diseases involving neovascularization. These diseases include a variety of cancers which rely on or are characterized by neovascularization, in addition to inflammatory diseases.

Human antibodies of the present invention also can be used to block or inhibit the effects of IL-15 associated with infectious diseases, such as HIV. Accordingly, another use for the antibodies of the invention includes the prevention or treatment of infectious diseases, e.g., HIV-1.

For example, the antibodies can be used in vitro or in vivo to diagnose a variety of diseases mediated by IL-15. Specifically, the antibodies can be used to detect levels of IL-15, or levels of cells which contain IL-15 on their membrane surface or linked to their receptors (receptor-bound human IL-15). The detection of such levels of IL-15 can then be correlated to certain disease symptoms. Alternatively, the antibodies can be used to inhibit or block IL-15 function which, in turn, can prevent or ameliorate disease symptoms caused by IL-15 function.

As previously described, human anti-IL-15 antibodies of the invention can be co-administered with one or other more therapeutic agents, e.g., an immunosuppressive agent or an anti-inflammatory agent to increase the overall anti-inflammatory effect. The antibody can be linked to the agent (as an immunocomplex) or can be administered separate from the agent. In the latter case (separate administration), the antibody can be administered before, after or concurrently with the agent. Suitable therapeutic agents include, among others, anti-inflammatory agents, DMARDs (disease-modifying anti-rheumatic drugs), immunosuppressive agents, chemotherapeutics, and psoriasis agents. The human antibodies according to the invention can also be administered in conjunction with radiation therapy.

In another embodiment, the human antibodies of the invention can be administered in combination with other antibodies, such as CD4 specific antibodies and IL-2 specific antibodies. A combination of the present human antibodies with CD4 specific antibodies or IL-2 specific antibodies are considered particularly useful for treating autoimmune diseases and transplant rejections.

Also within the scope of the present invention are kits comprising human anti-IL-15 antibodies of the invention and, optionally, instructions for use. The kit can further contain one or more additional reagents, such as an immunosuppressive reagent, or one or more additional human antibodies of the invention (e.g., a human antibody having a complementary activity which binds to an epitope in the IL-15 antigen distinct from the first human antibody).

Accordingly, patients treated with antibodies of the invention can be additionally administered (prior to, simultaneously with, or following administration of a human antibody of the invention) with another therapeutic agent, such as an anti-inflammatory agent, which enhances or augments the therapeutic effect of the human antibodies.

In yet another embodiment, human antibodies of the invention can be used to target compounds (e.g., therapeutic agents, labels, cytotoxins, immunosuppressants etc.) to cells which have IL-15 bound to their surface (e.g., membrane bound or bound to IL-15 receptor by linking such compounds to the antibody. Thus, the invention also provides methods for localizing ex vivo, in vivo or in vitro cells expressing IL-15 and IL-15 receptor (e.g., with a detectable label, such as a radioisotope, a fluorescent compound, an enzyme, or an enzyme co-factor).

Other embodiments of the present invention are described in the following Examples.

The present invention is further illustrated by the following examples which should not be construed as further limiting. The contents of Sequence Listing, figures and all references, patents and published patent applications cited throughout this application are expressly incorporated herein by reference.

EXAMPLES

Example 1

Generation of Cmu Targeted Mice

Construction of a CMD Targeting Vector

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in E. coli.

The targeting vector was constructed as follows. A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the Sma I site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65-74) and containing the pgk polyadenylation site (PvuII/HindIII fragment; Boer et al. (1990) Biochemical Genetics 28: 299-308). This cassette was obtained from the plasmid pKJ1 (described by Tybulewicz et al. (1991) Cell 65: 1153-1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al. (1988) Nature 336: 348-352. This cassette consists of the coding sequences of the tk gene bracketed by the mouse pgk promoter and polyadenylation site, as described by Tybulewicz et al. (1991) Cell 65: 1153-1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells

AB-1 ES cells (McMahon, A. P. and Bradley, A., (1990) *Cell* 62: 1073-1085) were grown on mitotically inactive SNL76/7 cell feeder layers (ibid.) essentially as described (Robertson, E. J. (1987) in *Teratocarcinomas and Embryonic Stem Cells: a Practical Approach* (E. J. Robertson, ed.) Oxford: IRL Press, p. 71-112). The linearized CMD targeting vector was electroporated into AB-1 cells by the methods described Hasty et al. (Hasty, P. R. et al. (1991) Nature 350: 243-246). Electroporated cells were plated into 100 mm dishes at a density of $1–2 \times 10^6$ cells/dish. After 24 hours, G418 (200 micrograms/ml of active component) and FIAU ($5 \times 10^{-7}$ M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described by Laird et al. (Laird, P. W. et al., (1991) Nucleic Acids Res. 19: 4293). Isolated genomic DNA was digested with SpeI and probed with a 915 bp SacI fragment, probe A (see FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated mu Gene

The three targeted ES clones, designated number 264, 272, and 408, were thawed and injected into C57BL/6J blastocysts as described by Bradley (Bradley, A. (1987) in *Teratocarcinomas and Embryonic Stem Cells: a Practical Approach*. (E. J. Robertson, ed.) Oxford: IRL Press, p. 113-151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647-656). Four agouti offspring were generated. Serum was obtained from these animals at the age of 1 month and assayed by ELISA for the presence of murine IgM. Two of the four offspring were completely lacking IgM (see Table 1). Genotyping of the four animals by Southern blot analysis of DNA from tail biopsies by BglI digestion and hybridization with probe A (see FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 1

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | 0.002 | JHD/JHD |

Table 1 shows the levels of serum IgM, detected by ELISA, for mice carrying both the CMD and JHD mutations (CMD/JHD), for mice heterozygous for the JHD mutation (+/JHD), for wild type (129SvxC57BL/6J)F1 mice (+/+), and for B cell deficient mice homozygous for the JHD mutation (JHD/JHD).

Example 2

Generation of HCO12 Transgenic Mice

The HCO12 Human Heavy Chain Transgene

The HCO12 transgene was generated by coinjection of the 80 kb insert of pHC2 (Taylor et al., 1994, Int. Immunol., 6: 579-591) and the 25 kb insert of pVx6. The plasmid pVx6 was constructed as described below.

An 8.5 kb HindIII/SalI DNA fragment, comprising the germline human $V_H$ 1-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human $V_H$ 5-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287-6295), to generate the plasmid p251f. A new cloning vector derived from pGP1f, pGP1k (SEQ ID NO:13), was digested with EcoRV/BamHI, and ligated to a 10 kb EcoRV/BamHI DNA fragment, comprising the germline human $V_H$ 3-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A clone was obtained with the $V_H$ 1-18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J×DBA/2J) F2 embryos as described by Hogan et al. (B. Hogan et al., Manipulating the Mouse Embryo, A Laboratory Manual, $2^{nd}$ edition, 1994, Cold Spring Harbor Laboratory Press, Plainview N.Y.). Three independent lines of transgenic mice comprising sequences from both Vx6 and HC2 were established from mice that developed from the injected embryos. These lines are designated (HCO12) 14881, (HCO12) 15083, and (HCO12) 15087. Each of the three lines were then bred with mice comprising the CMD mutation described in Example 1, the JKD mutation (Chen et al. 1993, EMBO J. 12: 811-820), and the (KCo5) 9272 transgene (Fishwild et al. 1996, Nature Biotechnology 14: 845-851). The resulting mice express human heavy and kappa light chain transgenes in a background homozygous for disruption of the endogenous mouse heavy and kappa light chain loci.

Example 3

Production of Human Monoclonal Antibodies Against IL-15

HCo12 and HCo7 transgenic mice, generated as described above and supplied from Medarex, San Jose, Calif., USA, were immunised with human recombinant IL-15 (hIL-15, Immunex corp., Seattle, USA) supplemented with either Complete Freunds Adjuvant (CFA, lot no. 121024LA, Difco Laboratories, Detroit, Mich., USA) or with Incomplete Freunds Adjuvant (ICFA, lot no. 121195LA, Difco, subcutaneously (SC) intraperitoneally (IP) or intravenously (IV). In several instances hIL-15 coupled to KLH was used for immunisation. After several boosts with hIL-15 supplemented with either Complete or Incomplete Freunds Adjuvant, the serum of the mice was tested for the presence of human antibodies directed against IL-15.

Immunisation Schemes of the Transgenic Mice which Resulted in Final Clones 146B7, 146H5, 404E4 and 404A8

| Mouse no. 146 (HCo12), ID 995-146, Female | | |
|---|---|---|
| 170699 | SC | 12 µg hIL-15 in CFA (Difco, Lot no. 121024LA) |
| 010799 | SC | 12 µg hIL-15 in ICFA (Difco, Lot no. 121195LA) |
| 150799 | SC | 12 µg hIL-15 in ICFA |
| 020899 | SC | 12 µg hIL-15-KLH in ICFA |
| 070999 | SC | 12 µg hIL-15-KLH in ICFA |
| 280999 | SC | 12 µg hIL-15-KLH in CFA |
| 111099 | IV | 30 µg hIL-15 in PBS |
| 121099 | IV | 30 µg hIL-15 in PBS |
| 151099 | | fusion of lymph node and spleen cells of this mouse with SP2/0 |

| Mouse no. 404 (HCo7), ID 997-404, Female | | |
|---|---|---|
| 201099 | IP | 25 µg hIL-15-KLH in CFA (Difco, lot no. 121024LA) |
| 031199 | IP | 12.5 µg hIL-15, 12.5 µg hIL-15-KLH, 25 µg in ICFA (Difco, lot no. 121195LA) |

-continued

| Mouse no. 404 (HCo7), ID 997-404, Female | | |
|---|---|---|
| 101199 | IV | 12.5 µg hIL-15, 12.5 µg hIL-15-KLH |
| 121199 | IV | 12.5 µg hIL-15, 12.5 µg hIL-15-KLH |
| 191199 | | fusion of lymph node and spleen cells of this mouse with SP2/0 |

Culture Media

Fusion Partner Medium (FPM):

Iscoves Modified Dulbecco's Medium was supplemented with 100 IU/ml penicillin, 100 µg/ml streptomycin, 1 mM Na-Pyruvate, 0.5 mM β-mercaptoethanol (Life Technologies, Paisley, Scotland) and 10% heat-inactivated fetal calf serum (HyClone, Utah, USA).

Fusion Selection Medium (FSM):

FPM supplemented with 30 ml Origen Hybridoma Cloning Factor (IGEN, Gaithersburg, Md., USA), HAT (1 vial, manufacturer's recommended concentration, Sigma Chemical Co., St. Louis, Mo., USA) and 0.5 mg/ml kanamycin (Life Technologies, Paisley, Scotland).

Fusion Cloning Medium (FCM):

FPM supplemented with 20 ml Origen Hybridoma Cloning Factor (IGEN, Gaithersburg, Md., USA), HT (1 vial, manufacturer's recommended concentration, Sigma Chemical Co., St. Louis, Mo., USA) and 0.5 mg/ml kanamycin (Life Technologies, Paisley, Scotland).

Hybridoma Preparation: Fusion of Spleen and Lymph Node Cells with SP2/0 Myeloma Cells To obtain hybridomas, spleen, inguinal and para-aortic lymph nodes were removed from the mice. Single cells suspensions of spleen and lymph node cells were mixed with SP2/0 myeloma cells in a cell ratio 1:2. Cells were spun down and the pellet was resuspended gently in 1 ml polyethyleneglycol (50% w/v in PBS, Sigma-Aldrich, Irvine, UK) at 37° C. After swirling the cells for 60 seconds, 25 ml FPM-2 was added and cells were incubated at 37° C. for 30-60 minutes. After incubation, cells were cultured at a cell concentration of $0.75 \times 10^5$ cells per well (in 100 µl) in 96-wells plates in FSM. After 3 days, 100 µl FSM was added to each well.

Fusion of spleen and lymph nodes of HCo7 and HCo12 mice immunised with hIL-15 resulted in the generation of several hybridomas producing antibodies directed against IL-15. The following four stable clones producing fully human anti-IL-15 antibodies were isolated: (1) 146LyD7F7B7 renamed: 146B7; (2) 146DE2E12A3H5 renamed: 146H5; (3) 404CG11B7E4 renamed: 404E4; and (4) 404FB12E7A8 renamed: 404A8. These clones were all of the human IgG1/k subclass.

Screening of the Hybridomas

Between day 7 and 11 after the fusion, the wells were screened for the presence of human antibodies using the following ELISAs:

ELISA to Screen for the Presence of Human IgG in the Culture Supernatants

To perform the ELISA to detect the presence of human IgG antibodies, 100 µl/well of 0.9 µg/ml rabbit-1-k-light chains antibodies (DAKO, Glostrup, Denmark) was added in phosphate buffered saline (PBS) to Nunc Maxisorp ELISA-plate (incubation overnight at room temperature). After blocking the plate with PBS supplemented with chicken serum (2%; Life Technologies, Paisley, Scotland) and Tween-20 (0.05%; PBSTC), culture supernatants were added. After incubation for 1.5 hour the plates were washed and rabbit-α-Human IgG (Fab2-fragments) conjugated with horse radish peroxidase (DAKO, Glostrup, Denmark) 0.5 µg/ml diluted in PBSTC was added. After incubation for 1 hour, the wells were washed and substrate, ABTS (2,2'-Azinobis-3-ethylbenzthiazoline-sulphonic-acid, Roche Diagnostics, Mannheim, Germany) was added according to the manufacturer's protocol and antibody binding was evaluated at 405 run in an EL808 ELISA-reader (Bio-tek Instruments, Winooski, Vt., USA).

ELISA to Screen for the Presence of IL-15 Specific Antibodies

Wells containing human IgG/k antibodies were further tested for the presence of human anti-IL-15 antibodies in an IL-15-specific ELISA. To perform the ELISA, 100 µl/well of 1 µg/ml IL-15 was added in phosphate buffered saline (PBS) to Nunc Maxisorp ELISA-plate (incubation overnight at room temperature). After blocking the plate with PBS supplemented with chicken serum (2%; Life Technologies, Paisley, Scotland) and Tween-20 (0.05%; PBSTC), culture supernatants were added. After incubation for 1.5 hours the plates were washed and α-Human IgG Fc conjugated with horse radish peroxidase (Jackson Immuno research, West Grove, Pa., USA) 1/5000 diluted in PBSTC was added. After incubation for 1 hour, the wells were washed and substrate, ABTS (2,2'-Azinobis-3-ethylbenzthiazoline-sulphonic-acid, Roche Diagnostics, Mannheim, Germany) was added according to the manufacturer's protocol and antibody binding was evaluated at 405 nm in an EL808 ELISA-reader (Bio-tek Instruments, Winooski, Vt., USA).

Subcloning of the Hybridomas

To obtain stable anti-IL-15 cell lines, the hybridomas were subcloned by a limiting dilution of the cells (to 0.5 cell/well) in 96-wells plates.

The subclones were tested after approximately 10 days with the above mentioned IL-15 ELISA. During the several subcloning procedures, FSM was changed in phases via FCM to FPM. The isotype of the subclones was determined with the ELISA described below.

Isotype Determination of the Anti-IL-15 Antibodies by ELISA

To perform the isotype ELISA, 1001/well of 1 µg/ml anti-human Fc (Jackson Immuno research) was added in phosphate buffered saline (PBS) to Nunc Maxisorp ELISA-plate (incubation overnight at room temperature). After blocking the plate with PBS supplemented with chicken serum (2%; Life Technologies, Paisley, Scotland) and Tween-20 (0.05%; PBSTC), culture supernatants were added. After incubation for 1.5 hours the plates were washed and mouse-α-HuIgG1 conjugated with alkaline phosphatase (Zymed, plaats, land), or mouse-α-HuIgG3 conjugated with horse radish peroxidase (Zymed) was added. After incubation for 1 hour the wells were washed and substrate, ABTS (2,2'-Azinobis-3-ethylbenzthiazoline-sulphonic-acid, Roche Diagnostics, Mannheim, Germany) was added according to the manufacturer's protocol. Antibody binding was evaluated at 405 nm in an EL808 ELISA-reader (Bio-tek Instruments, Winooski, Vt., USA.

Example 4

Epitope Specificity of Fully Human Anti-IL-15 Antibodies

To function therapeutically and to inhibit IL-15-induced proinflammatory effects, IL-15 specific antibodies need to recognize the IL-15 epitopes involved in interaction with the IL-2Rβ-chain and/or the γ-chain of IL-15 receptor.

Mutant proteins (described by Pettit et al.) were used to evaluate the epitope specificity of the fully human anti-IL-15 antibodies, 146B7, 146H5, 404A8 and 404E4. The IL-15 mutants used include IL-15 mutant Q108S (Gln at residue 108 was replaced by Ser; a mutation in the γ-chain interaction site) and mutant D8SQ108S (Gln at residue 108 was replaced by Ser and Asp at position 8 was substituted for Ser; mutations in both the β and γ-chain interaction sites of IL-15).

ELISA to Determine Binding of the hIL-15 Specific Antibodies, 146B7, 147H5, 404A8 and 404E4, to hIL-15 and to Mutant IL-15 Proteins To perform the ELISA, 100 µl of 1 µg/ml IL-15 or hIL-15 mutant protein, in phosphate buffered saline (PBS), was added to Nunc Maxisorp ELISA-plate for coating. After blocking the plate with PBS supplemented with chicken serum (2%; Life Technologies, Paisley, Scotland) and Tween-20 (0.05%; PBSTC), serial dilutions of the hIL-15 specific antibodies were incubated. After washing, α-Human IgG Fc conjugated with peroxidase (Jackson Immuno research, West Grove, Pa., USA) 1/5000 diluted in PBSTC was added. After washing substrate, ABTS (2,2'-Azinobis-3-ethylbenzthiazoline-sulphonic-acid, Roche Diagnostics, Mannheim, Germany) was added according to the manufacturer's protocol and antibody binding was evaluated at 405 nm in an EL808 ELISA-reader (Bio-tek Instruments, Winooski, Vt., USA).

The binding of the fully human IL-15 specific antibodies 146B7, 146H5, 404A8 and 404E4 to hIL-15 and to the IL-15 mutant proteins Q108S and D8SQ108S is shown in FIG. 1. Neither 146B7 nor 146H5 were able to bind to these mutant IL-15 proteins. Since both mutants carry the Q108S mutation, the epitope recognized by 146B7 and 146H5 is within the critical domains of IL-15 which interact with the γ-chain of the IL-15 receptor. 404A8 and 404E4 were both able to bind the mutant proteins, therefore, these antibodies recognize an epitope outside the β- and γ-chain interacting domains of IL-15. Both 146B7 and 146H5 bind to IL-15 at the region that interacts with the γ-chain of the IL-15 receptor. This agrees with the data obtained from the proliferation assays using the fully human anti-IL-15 antibodies of the present invention. As described in detail below, neither 404A8 nor 404E4 were able to inhibit IL-15-induced proliferation of CTLL-2 cells and human PBMCs. Both 146B7 and 146H5 were able to inhibit IL-15-induced proliferation. Further, inhibition of proliferation is achieved by blocking the interaction of IL-15 with the γ-subunit of the IL-15 receptor.

Example 5

$V_H$ and $V_L$—Region Sequences of 146B7

The nucleotide and deduced amino acid sequence of rearranged $V_H$ and $V_L$-domains of 146B7 were determined using the following procedures. These sequences give information regarding the $V_H$ and $V_L$ germline families used; point mutations in these germline sequences are due to affinity maturation of B-cells during the immunization of the animal.

RNA Preparation

Total RNA was prepared from 5×10$^6$ 146B7 hybridoma cells with RNAzol (Biogenesis, Poole, England) according to the manufactures protocol.

cDNA Preparation

The cDNA of RNA from 146B7 was prepared from 3 µg total RNA with AMV Reverse Transcriptase with buffer (Roche Diagnostics GmbH, Mannheim, Germany), oligo d(T)$_{15}$ (Promega, Madison, Wis., USA), dNTP (Boehringer Mannheim corp., USA) and RNAsin (Promega) according to the manufacturer's protocol.

PCR Primers Used to Amplify $V_H$ and $V_L$ Regions for Cloning

Primer pairs used:

VH:

FR1 5' primers (1) AB62    CAg gTK CAg CTg gTg CAg TC
(2) AB63    SAg gTg CAg CTg KTg gAg TC
(3) AB65    gAg gTg CAg CTg gTg CAg TC $V_H$ leader 5' primers (4) AB85    ATg gAC Tgg ACC Tgg AgC ATC
(5) AB86    ATg gAA TTg ggg CTg AgC Tg
(6) AB87    ATg gAg TTT ggR CTg AgC Tg
(7) AB88    ATg AAA CAC CTg Tgg TTC TTC
(8) AB89    ATg ggg TCA ACC gCC ATC CT $V_H$ 3' primer (9) AB90    TgC CAg ggg gAA gAC CgA Tgg $V_K$:

FR1 5' primers (1) AB8     RAC ATC CAg ATg AYC CAg TC
(2) AB9     gYC ATC YRg ATg ACC CAg TC
(3) AB10    gAT ATT gTg ATg ACC CAg AC
(4) AB11    gAA ATT gTg TTg ACR CAg TC
(5) AB12    gAA ATW gTR ATg ACA CAg TC
(6) AB13    gAT gTT gTg ATg ACA CAg TC
(7) AB14    gAA ATT gTg CTg ACT CAg TC $V_K$ leader 5' primers:

(8) AB123   CCC gCT Cag CTC CTg ggg CTC CTg
(9) AB124   CCC TgC TCA gCT CCT ggg gCT gC
(10) AB125  CCC AgC gCA gCT TCT CTT CCT CCT gC
(11) AB126  ATg gAA CCA Tgg AAg CCC CAg CAC AgC $V_K$ 3' primer

(12) AB16   Cgg gAA gAT gAA gAC AgA Tg

PCR Conditions Used to Amplify $V_H$ and $V_L$ Regions for Cloning

PCR Reactions were performed with AmpliTaq polymerase (Perkin Elmer) on a GeneAmp PCR System 9700 (Perkin Elmer Applied Biosystems, Foster City, Calif., USA).

PCR Cycling Protocol:

| | |
|---|---|
| 11 cycles | 94° 2' |
| | 94° 30" |
| | 65° 30", minus 1° per cycle |
| | 72° 30" |
| 30 cycles | 94° 30" |
| | 55° 30" |
| | 72° 30" |
| | 72° 10' |
| | cool down to 4° |

Cloning of $V_H$ and $V_L$ in pGEMT-Vector System I

After analysing the PCR products on an agarose gel, the products were purified with S-400 or S300 microspin columns (Amersham Pharmacia Biotech Inc., Piscataway, N.J., USA), or with the QIAEX II Gel Extraction Kit (Qiagen GmbH, Hilden, Germany). For each experiment 2 independently amplified PCR products, using FR1 or leader primers, of each $V_H$ and $V_L$ region were cloned in pGEMT-Vector System I (Promega) according to manufacturers protocol.

After transformation to *E. coli* DH5α, individual colonies were screened by colony PCR using T7 and SP6 primers, 30 cycles at 55°. Plasmid DNA from each individual colony was purified using Qiaprep Spin miniprep kit (Qiagen). To further analyze a Nco1/Not1 (NE Biolabs, United Kingdom and Roche Diagnostics) digestion was performed and analyzed on agarose gel.

Sequencing

The V-regions were sequenced after cloning in the pGEMT-Vector System I. T7 and Sp6 primers (Eurogentec, Luik, Belgium) were used in combination with the sequence kit: ABI Prism BigDye Terminator Cycle Sequencing Ready Reaction Kit (Applied Biosystems, Warrington, United Kingdom) according to protocol. The reactions were performed on a ABI PRISM 377 Sequencer (PE Applied Biosystems) and the sequences were analysed with the program DNAStar, SeqmanII. The sequences were then aligned to germline V-gene sequences in VBASE (www.mrc-cpe.cam.ac.uk/imt-doc/public/intro.htm).

Cloning and Sequencing of the $V_H$ and $V_L$-Region of 146B7

$V_H$ and $V_L$-regions from hybridoma 146B7 were amplified by PCR and cloned in pGEMT-Vector System I to determine the cDNA-sequence. The nucleotide and corresponding amino acid sequences are shown in FIG. 2 (SEQ ID NOs: 1 and 2) and FIG. 3 (SEQ ID NOs: 3 and 4), respectively. The framework (FR) and complementarity determining regions (CDR) are also indicated. The germline family for the $V_H$-region of 146B7 according to alignment in Vbase: $V_H$5-51 ($V_H$5-subgroup), D2-15/D2 ($D_H$-segment), JH4b ($J_H$-segment). The germline family for the $V_L$-region of 146B7 according to alignment in Vbase: A27 ($V_K$III-subgroup) and $J_K$2 ($J_K$-segment). More information regarding $V_H$ and $V_L$-domains is shown at the Kabat database http://immuno.b-me.nwu.edu/or at http://www.Vbase.com.

Example 6

Affinity Binding Characteristics of 146B7

The affinity of 146B7 was analyzed by surface plasmon resonance (SPR) technology using a BIACORE 3000 instrument to determine biomolecular protein interactions according to the following procedures. Changes in the SPR signal on the surface layer caused by biomolecular binding are detected and signify a change in the mass concentration at the surface layer. Affinity is expressed using the following definitions: $k_a$=association rate constant ($M^{-1}$ $sec^{-1}$); $k_d$=dissociation rate constant ($sec^{-1}$); $K_A$=association equilibrium constant=$k_a/k_d$ ($M^{-1}$); and $K_D$=dissociation equilibrium constant=$k_d/k_a$ (M).

Different procedures were performed to obtain the affinity of 146B7 for human IL-15 (hIL-15). Human recombinant IL-15 from two different suppliers (Immunex corp., Seattle, USA and Peprotech, Rocky Hill, N.J., USA) was coupled to a CM5 sensor chip. The compound coupled to the sensorchip is defined as ligand. In other experiments 146B7 was used as ligand.

In each kinetic analysis, the binding of the analyte, 146B7 or hIL-15 adapted to the ligand coupled to the sensorchip, was compared to the binding to a reference control CM5 sensor chip. Serial dilutions of analyte were tested (0, 3.125, 6.25, 12.5, 25, 50 µg/ml). Association and dissociation curves were fitted for monomeric interaction in the model Langmuir 1:1, to determine $k_a$ and $k_d$ and to calculate $K_A$ and $K_D$. All data were analyzed using BIA-Evaluation Version 3.1. For a bivalent interaction the model "bivalent analyte" was used. All analysis were corrected for a drifting baseline.

To determine the antibody affinity of 146B7, the affinity of antibody 146B7 was measured for human recombinant IL-15 derived from two different suppliers, Immunex and Peprotech, at the BIACORE 3000. Using 146B7 as ligand and hIL-15 as analyte, the monovalent interaction was determined (curve fitting Langmuir 1:1).

The affinity of 146B7 for IL-15 (Immunex Corp.) was measured as follows:

The association rate constant $k_a$: 1.07 (±0.17)×$10^5$ $M^{-1}$ $sec^{-1}$

The dissociation rate constant $k_d$: 6.56 (±0.09)×$10^{-3}$ $sec^{-1}$

Association equilibrium constant $K_A$: 1.55 (±0.21)×$10^{-7}$ $M^{-1}$

Dissociation equilibrium constant $K_D$: 6.59 (±0.88)×$10^{-8}$ M

To determine the avidity of 146B7, IL-15 (Immunex Corp.) was used as ligand and 146B7 was used as analyte. When the data obtained were analyzed using Langmuir (1:1) curve fitting the bivalent interaction of the antibody was expressed, the avidity of the antibody was determined.

The avidity of 146B7 for IL-15 (Immunex Corp.) was measured as follows:

The association rate constant $k_a$: 7.30 (±0.81)×$10^5$ $M^{-1}$ $sec^{-1}$

The dissociation rate constant $k_d$: 1.45 (±2.05)×$10^{-3}$ $sec^{-1}$

Association equilibrium constant $K_A$: 5.03 (±3.40)×$10^8$ $M^{-1}$

Dissociation equilibrium constant $K_D$: 1.55 (±1.24)×$10^{-9}$ M

The affinity and avidity of 146B7 for Peprotech derived IL-15 were determined also. No major differences in affinity or avidity for two different sources of IL-15 were seen.

As is described in the example below regarding the inhibition of human interleukin-15 (hIL-15)-induced proliferation of CTLL-2 cells and PBMC by fully human anti-IL-15 antibodies, 146B7 inhibited in a dose dependent manner the IL-15 induced proliferation as was measured by [$^3$H]-thymidine incorporation. The IC50-concentration at 50% inhibition, a more functional manner to determine affinity-from these proliferation inhibition experiments was calculated: 3.1±0.91 nM. This IC50 is in agreement with the avidity measured by BIACORE 3000 ($K_D$ 1.5 nM) using 146B7 as ligand and recombinant human IL-15 as analyte and confirmed the affinity and avidity measurements obtained here.

Example 7

Inhibition of hIL-15-Induced TNF-α Production by Fully Human Anti-IL-15 Antibodies The effect of fully human anti-IL-15 antibodies, 146B7, 146H5, 404E4 and 404A8, on IL-15-induced TNF-α production was studied using peripheral blood derived mononuclear cells (PBMC) from healthy volunteers using the following procedures. To evaluate specificity to IL-15, the effect of these antibodies on IL-2-mediated TNF-α production was also examined.

Cell Culture

Cultures were maintained in RPMI-1640 with 2 mM L-glutamine, 100 IU/ml penicillin, 100 µg/ml streptomycin (all derived from Life Technologies, Paisley, Scotland) and 10% heat-inactivated fetal calf serum (HyClone, Utah, USA).

Purification of Peripheral Blood Mononuclear Cells (PBMC)

Fresh human blood was drawn from a healthy volunteer after informed consent, heparin was added against coagulation. Purification of PBMC was performed by density gradient centrifugation using Ficoll (Pharmacia, Uppsala, Sweden).

Test Compound

HIL-15, lot no: 6870-011, Immunex corp., Seattle, Wash., USA.

hIL-2, Chiron Benelux B V, Amsterdam, The Netherlands.

Fully human antibodies used: 146B7 (batch: 070101) and 146B7RDJW07, 404A8 (batch: 030101) and 404E4 (batch: 080101) and as isotype control antibody T1 (97-2B11-2B12, batch: 190900).

Inhibition of Human IL-15 (hIL-15) or hIL-2-Induced TNF-α Production by PBMC by Anti-IL-15 Antibodies PBMC were cultured in triplicate or quadruplicate in 96-well flat-bottom plate at 1.5×$10^5$ cells per well in the presence or absence of hIL-2 or hIL-15 and with or without anti-IL-15 antibodies. Isotype control antibody (T1) was included as negative control. Concanavalin A (2.5 µg/ml, Calbiochem) was added as a positive control for proliferation. Cells were incubated for 72 hours at 37° C. and 5% $CO_2$. Supernatants were harvested to quantify the amount of human TNF-α by ELISA (U-CyTech, Utrecht, The Netherlands).

The effects of 146B7 and an isotype control antibody were tested on IL-15-mediated TNF-α production by PBMC. 146B7 inhibited hIL-15-mediated TNF-α production in a dose dependent fashion, whereas the isotype control antibody did not inhibit hIL-15-induced TNF-α production (FIG. 4). Data of two healthy volunteers are shown. 404E4 and 404A8 were unable to inhibit hIL-15-induced TNF-α production.

Figure 5:
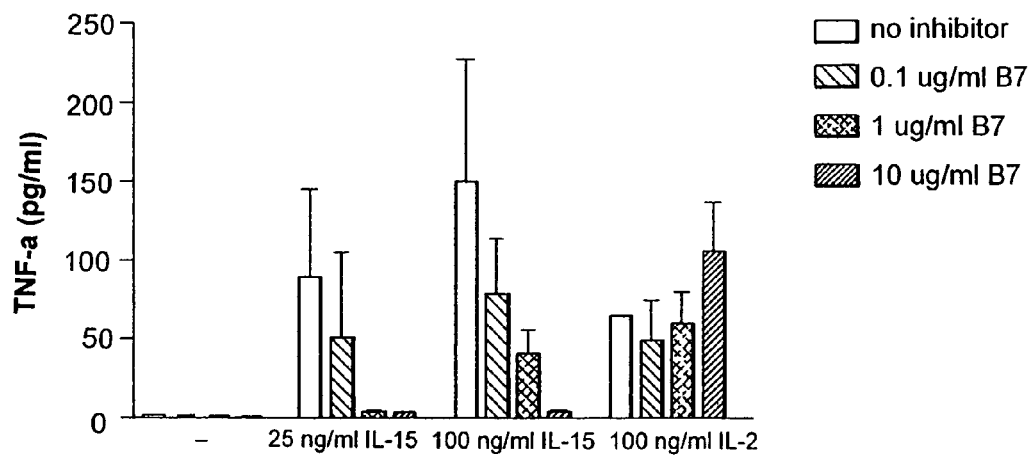
FIG. 5 is a graph showing the effect of antibody 146B7 on IL-2 or IL-15-mediated TNF-α production. Human PBMC were incubated with hIL-15 (0, 50, 100 ng/ml) or with hIL-2 (100 ng/ml) in combination with 146B7 (0.1, 1, 10 µg/ml) for 72 hours. The amount of TNF-α produced was measured by ELISA.

To ensure the specificity of the anti-IL-15 antibodies, their effect on hIL-2-mediated TNF-α production was evaluated. No inhibition of IL-2-mediated TNF-α production was induced by 146B7 (FIG. 5). No dose dependent inhibition by either 404E4 or 404A8 was seen in hIL-2-mediated TNF-α production.

A dose dependent inhibition of hIL-15-mediated TNF-α production was seen only by 146B7 and not by 404E4 and 404A8. The inhibitory effect was specific for hIL-15; IL-2-mediated TNF-α production was not inhibited.

Example 8

Inhibition of Human Interleukin-15 (hIL-15)-Induced Proliferation of CTLL-2 Cells and PBMC by Fully Human Anti-IL-15 Antibodies Antibodies 146B7, 146H5, 404E4 and 404A8 were tested for their ability to inhibit T-cell proliferation using CTLL-2 cells (Gillis et al., 1978) and peripheral blood mononuclear cells (PBMC) using the following procedures.

Cell Culture

Cultures were maintained in RPMI-1640 with 2 mM L-glutamine, 100 IU/ml penicillin, 100 µg/ml streptomycin (derived from Life Technologies, Paisley, Scotland) and 10% heat-inactivated fetal calf serum (HyClone, Utah, USA). CTLL-2 cells (Gillis et al., 1978) were maintained in the above mentioned medium supplemented with 36 units hIL-2/ml (Chiron Benelux B V, Amsterdam, The Netherlands) and starved for hIL-2 for 3-4 days before the start of the experiment. CTLL-2 cells were washed three times before use.

Purification of Peripheral Blood Mononuclear Cells (PBMC)

Fresh human blood was drawn from a healthy volunteer after informed consent, heparin was added against coagulation. Purification of PBMC was performed by density gradient centrifugation using Ficoll (Pharmacia, Uppsala, Sweden).

Test Compound

Figure 6:
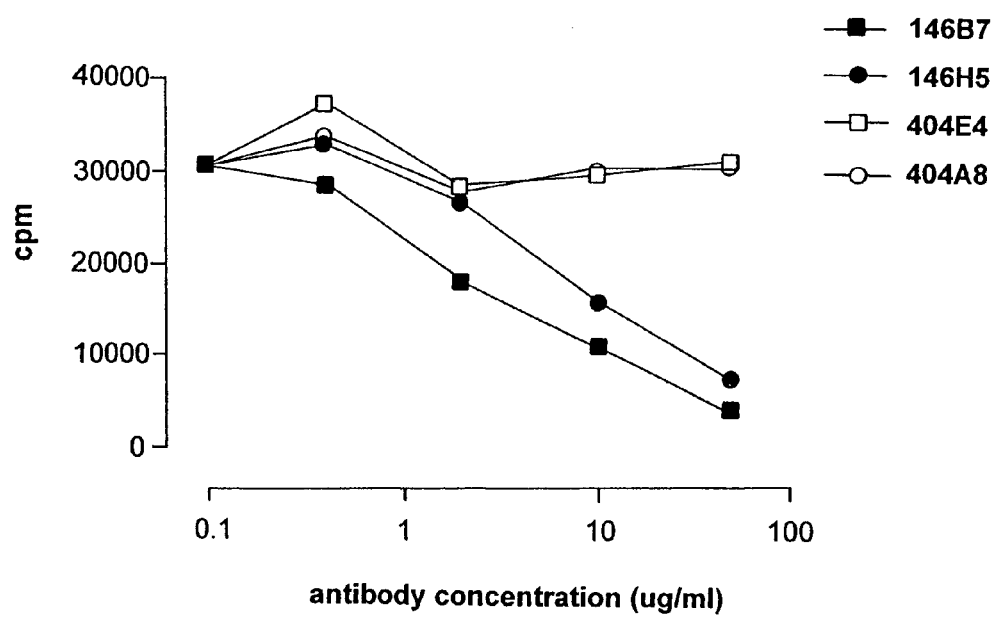
FIG. 6 is a graph showing the inhibitory activity of antibodies 146B7, 146H5, 404E4 and 404A8 on hIL-15 induced CTLL-2 proliferation. CTLL-2 cells starved for hIL-2 were incubated with hIL-15 (60 pg/ml) combined with serial dilutions of 146B7, 146H5, 404E4 and 404A8 for 48 hours. [$^3$H]-Thymidine incorporation was measured to express proliferation (cpm). The results are presented as mean values.

HIL-15, lot no: 6870-011, Immunex corp., Seattle, Wash., USA.

hIL-2, Chiron Benelux B V, Amsterdam, The Netherlands.

anti-IL-15 antibodies used for CTLL-2 assay in this report shown in FIG. 6: 146B7, 146H5, 404A8, 404E4.

anti-IL-15 antibodies used for PBMC assays: 146B7 (batch: 070101), 404A8 (batch: 030101) and 404E4 (batch: 080101).

Inhibition of Human IL-15 (hIL-15) or hIL-2 Induced CTLL-2 Proliferation by Anti-IL-15 Antibodies In each experiment, cells were seeded in triplicate in 96-well plate, $5\times10^3$ cells per well in the presence or absence of either hIL-2 or hIL-15. To evaluate the effect on proliferation, each of the four anti-IL-15 antibodies were added. Cells were incubated for 16 hours at 37° C. and 5% $CO_2$. [$^3$H] Thymidine (1 µCi/well, Amersham Life Sciences, Little Chalfont, Buckinghamshire, UK) was added 4 hours before harvesting (Harvester 96 Mach II M, Tomtec, Orange Conn., USA).

As is shown in FIG. 6, IL-15 induced proliferation of CTLL-2 cells was decreased in a dose dependent fashion by 146B7 and 146H5 as was reflected by reduced [$^3$H]-Thymidine incorporation. Both 404E4 and 404A8 were unable to block IL-15 induced proliferation of CTLL-2 cells.

Inhibition of hIL-15 (hIL-15) or hIL-2 Induced PBMC Proliferation by Anti-IL-15 Antibodies PBMC were cultured in triplicate in 96-well U-bottom plate (Nunc, Nalge Nunc International, Denmark), $5\times10^4$ cells per well in the presence or absence of hIL-2 or hIL-15 and the anti-IL-15 antibodies. Concanavalin A (2.5 µg/ml, Calbiochem) was added as a positive control for proliferation. The cells were incubated for 72 hours at 37° C. and 5% $CO_2$. [3H]Thymidine (1 µCi/well, Amersham Life Sciences, Little Chalfont, Buckinghamshire, UK) was added 16 hours before harvesting (Harvester 96, Tomtec, Orange Conn., USA).

Figure 7A:
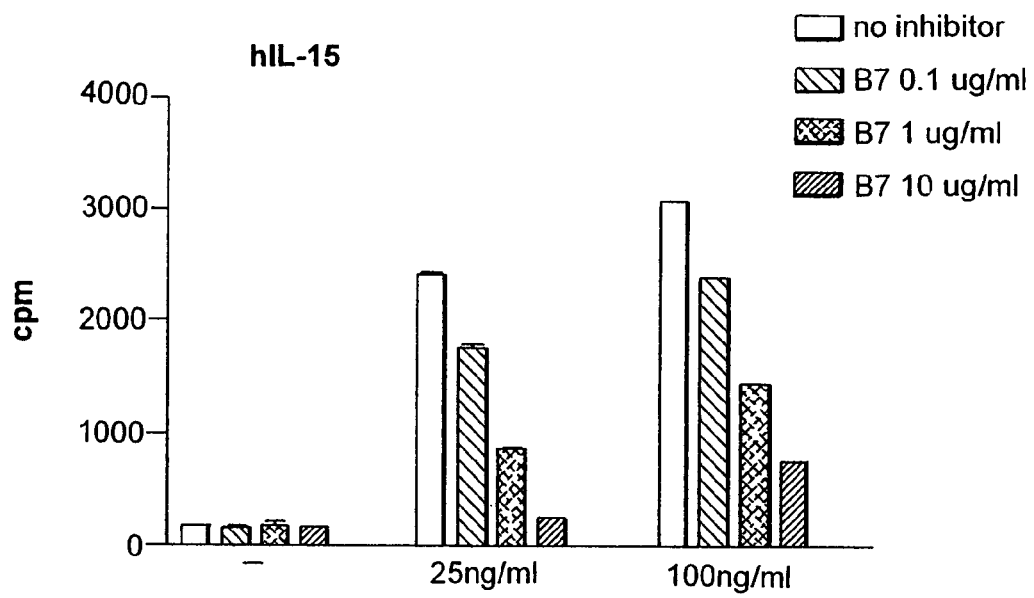
FIGS. 7A, 8A, and 9A, respectively) or hIL-2 (0, 10, 100 ng/ml.
Figure 7B:
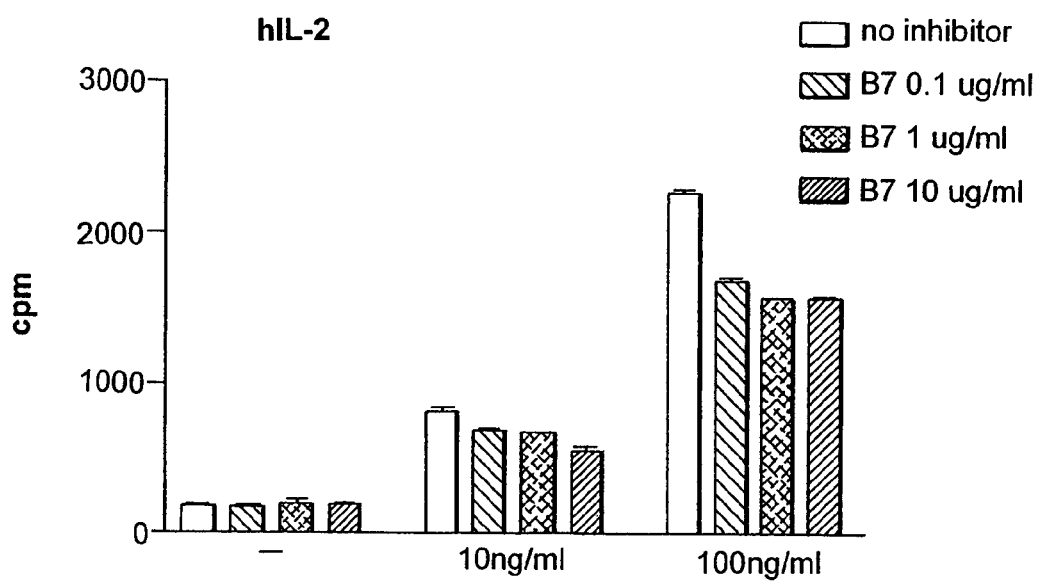
FIGS. 7B, 8B, and 9B, respectively) in combination with 146B7 (FIG. 7), 404E4 (FIG. 8) or 404A8 (FIG. 9) at 0.1, 1, 10 µg/ml for 72 hours. [3H]-Thymidine incorporation was measured to express proliferation (cpm).

146B7 was able to inhibit IL-15 induced [$^3$H]-Thymidine incorporation dose dependently and, therefore, inhibited proliferation (IC50=3.1±0.91 nM) (FIG. 7). Both 404E4 and 404A8 were unable to block hIL-15 induced PBMC proliferation (FIGS. 8-9). 146H5 was not tested according to data obtained from previously performed experiments.

Figure 8A:
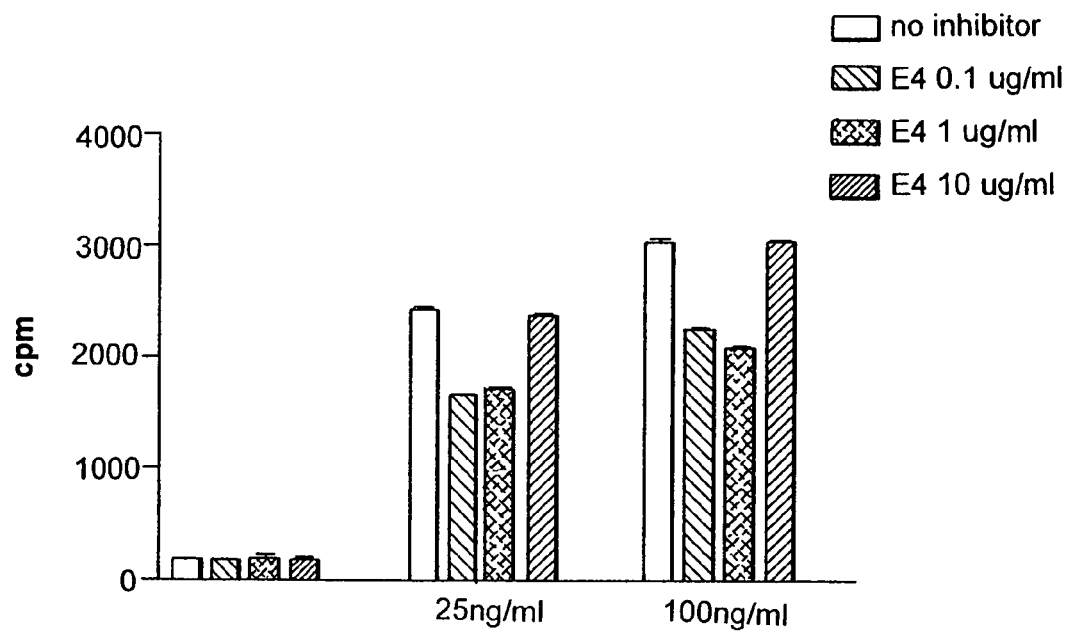
Figure 8B:
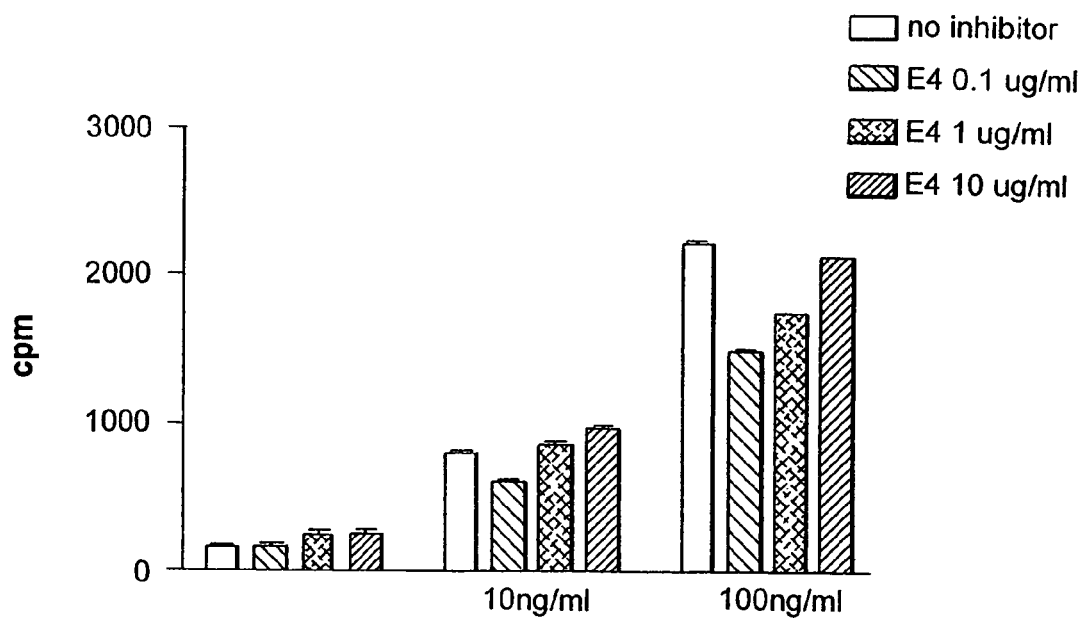
Figure 9A:
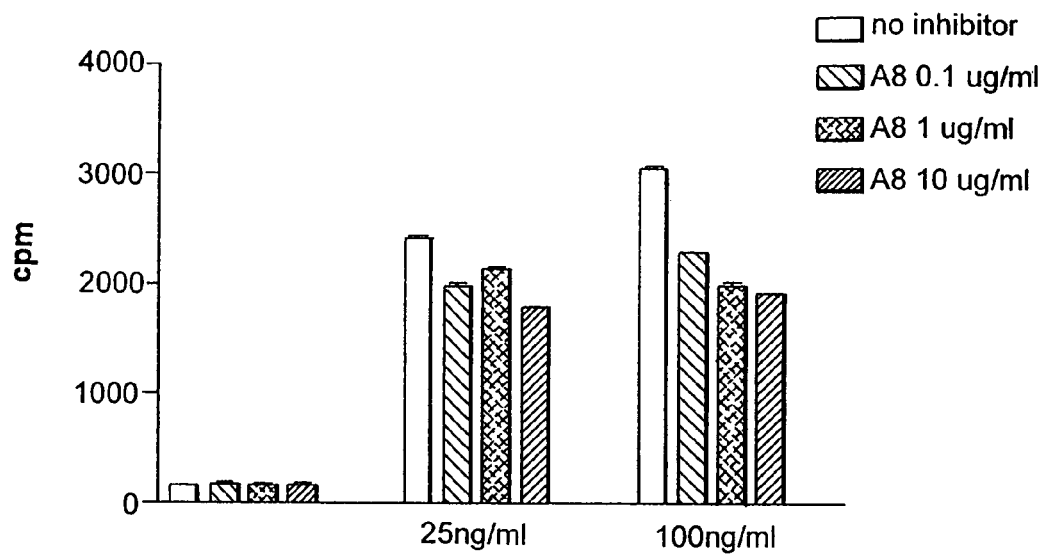
Figure 9B:
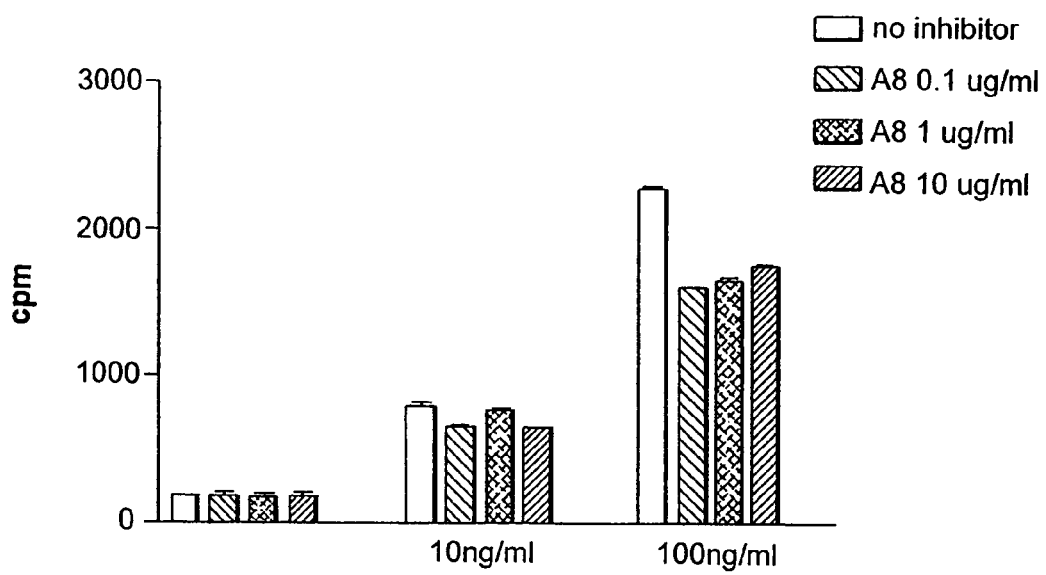

To ensure the specificity of 146B7, 404E4 and 404A8 for IL-15, these antibodies were also evaluated for their effects on IL-2 mediated proliferation. None of the tested anti-IL-15 antibodies exhibited an effect on IL-2 induced proliferation (FIGS. 7-9).

Example 9

Human Anti-IL-15 Antibody 146B7 Binds to Human IL-15 Present on Human PBMCs

Test Compounds

Human PBMCs were obtained from healthy volunteers after informed consent.

Antibody 146B7 (batch no. MDX015), Medarex Inc., Annandale, N.J., USA.

Biotinylation of 146B7 and Human IRG

N-hydroxysuccinimido-biotin (Sigma) was first diluted in DMSO (final dilution: 100 mg/ml) and then in 0.1 M $NaHCO_3$ (final dilution: 1 mg/ml, Sigma). Per 1 mg of antibody (diluted in 1 ml), 600 µl of biotin solution was added (dark, 2 hrs, RT). Antibody-biotin solution was dialysed in a Slide-a-lyzer™ dialysis cassette (10,000 MWCO, Pierce, Perbio Science, Netherlands) (overnight at 4° C.) to remove unlabeled biotin. The following day, concentration of biotinylated antibodies was determined by spectrophotometry (Ultrospec 2100pro) at OD 280 nm.

Stimulation of Peripheral Blood

To induce IL-15, blood was obtained by venapuncture from healthy volunteers. PBMCs were cultured in RPMI 1640 (Biowhittaker Europe) supplemented with penicillin (5 U/ml), streptomycin (50 µg/ml), L-glutamine (2 mM) (Biowhittaker Europe), and 10% fetal calf serum (Optimum C241, Multicell, Wisent Inc.) for a maximum of 2 days (37° C.), and were stimulated with 500 U/ml IFNγ (Boehringer Ingelheim).

Flow Cytometry

Cells were pre-incubated with 10% human AB serum (CLB, Amsterdam, Netherlands) in RPMI 1640 (Biowhittaker Europe) supplemented with penicillin (5 U/ml), streptomycin (50 µg/ml), L-glutamine (2 mM) (Biowhittaker Europe) and 10% fetal calf serum (Optimum C241, Multicell, Wisent Inc.). After permeabilization (20 min, 4° C., in Cytofix/Cytoperm™ Kit, Becton Dickinson, San Diego, Calif.) and washing in Perm/Wash™ buffer (Cytofix/Cytoperm™ Kit), PBMC were subjected to staining of IL-15 by flow cytometry. Continuous permeability was achieved by using Perm/Wash™ buffer (Cytofix/Cytoperm™ Kit) throughout the staining procedure. After incubating the cells with biotinylated 146B7 or with biotinylated hIgG1 (20 µg/ml, 30 min, 4° C.) and washing in Perm/Wash™ buffer, cells were subsequently incubated with streptavidin-phycoerythrin (DAKO) for 30 minutes (4° C.). Fluorescence intensity of at least 5000 cells per sample was determined after analysis by flow cytometry (FACS Calibur, Becton Dickinson) and gating on the monocytes, using CellQuest Pro software. Data show the stimulation index (S.I.), which is calculated as follows:
S.I.=(mean fluorescence positive staining)/(mean fluorescence background staining)

Immunocytochemistry

To detect IL-15 present in human monocytes, cytospin preparations were made of whole blood samples. After spinning down $5 \times 10^4$ cells (200 μl) onto Superfrost®-Plus microscope slides (Menzel), slides were air-dried (<60 min), fixed in 2% paraformaldehyde/PBS (8 min, 4° C.), washed with PBS and air-dried again. Before staining, cytospin preparations were permeabilized in PBS (+0.1% saponine; PBSS), which was subsequently used throughout the staining procedure. To block endogenous peroxidase activity, cytospin preparations were incubated with 0.05% (v/v) hydrogen peroxide ($H_2O_2$) diluted in citric acid/phosphate buffer (pH 5.8, 20 min, RT). After washing with PBSS, endogenous biotin activity was blocked according to the manufacturer's instructions (Biotin Blocking Kit, Vector Lab., DAKO). After washing with PBSS, non-specific binding sites were blocked by incubating the cytospin preparations with 10% (v/v) human pooled AB-serum (CLB, Amsterdam, Netherlands) (30 min) in PBSS. Thereafter, cytospin preparations were incubated with biotinylated primary antibody (60 min, RT) and, after washing with PBSS, with streptavidin complexed with biotinylated horseradish peroxidase (streptABComplex/HRP, DAKO; 1:100 in PBSS, containing 2% human AB serum; 30 min, RT). After washing in PBSS, the cytospin preparations were incubated with 3-amino-9-ethylcarbazole (0.5 mg/ml) and $H_2O_2$ (0.01%), in sodium acetate buffer (50 mM, pH 4.9) for 10 minutes (RT), for the detection of HRP activity. Cytospins were washed with running tap water for 5 minutes, counterstained with haematoxylin (DAKO) for one minute, washed with running tap water for another 5 minutes, and embedded in faramount or glycergel (DAKO).

Flow Cytometry

Figure 10:
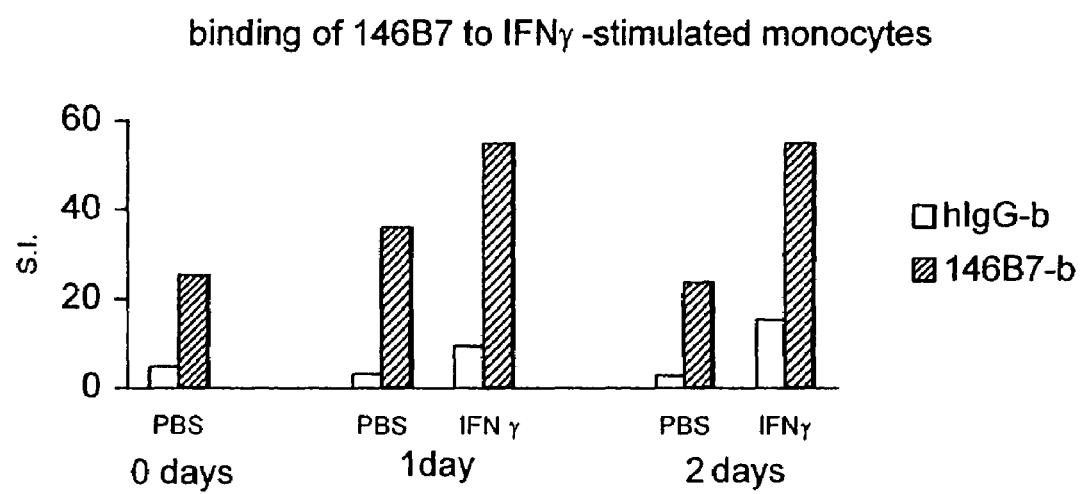
FIG. 10 is a graph showing the binding of antibody 146B7 to IFNγ-stimulated monocytes. Human PBMCs were cultured in the presence of IFNγ (500 U/ml) for up to 2 days (37° C.). Fluorescence intensity of at least 5000 cells per sample was determined after analysis by flow cytometry and gating on the monocytes. Data show the stimulation index (S.I.= (mean fluorescence positive staining)/(mean fluorescence background staining)).

Binding of 146B7 to IFNγ-stimulated human monocytes is shown in FIG. 10. Biotinylated 146B7 binds to unstimulated monocytes showing the presence of IL-15 in unstimulated cells. Stimulation of monocytes with IFNγ leads to a increased binding of 146B7 to the cells, with a maximum reached at day one of culture. The control antibody, hIgG1, shows little binding to unstimulated monocytes. Stimulation with IFNγ increases binding of hIgG1 through increased expression of Fcγ receptors on monocytes.

Immunocytochemistry

Figure 11B:
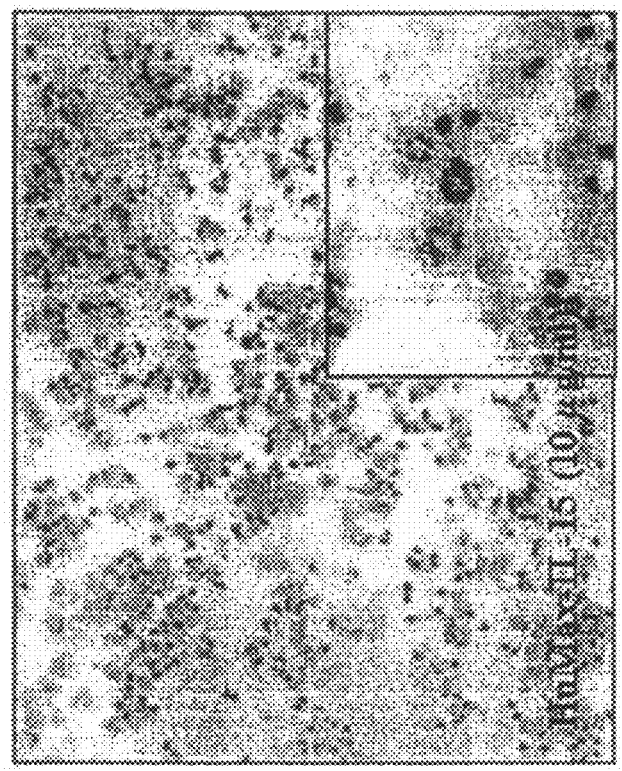
FIG. 11 shows binding of human monocytes with antibody 146B7 (panel B) or with the isotype control antibody (panel A). Human PBMCs were isolated and cytospins were made after culturing the cells with IFNγ (500 U/ml). Cells were counterstained with haematoxylin.
Figure 11A:
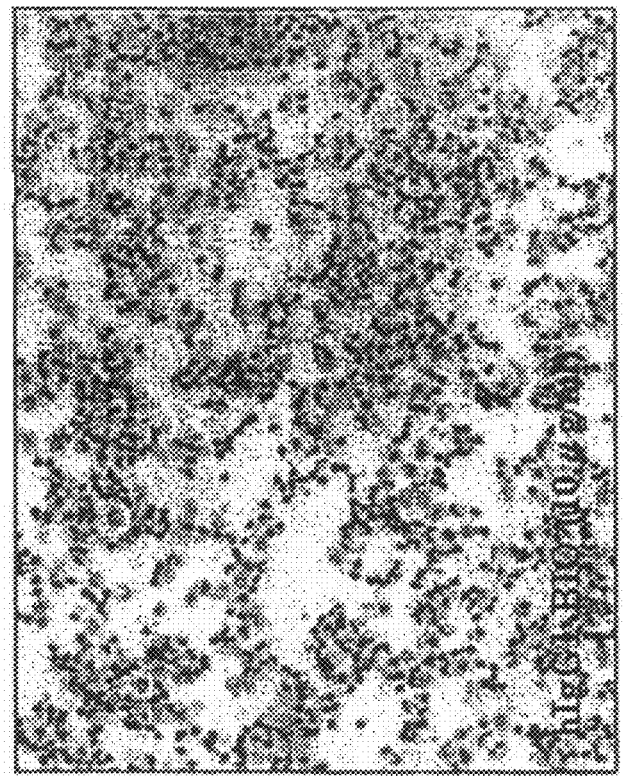

FIG. 11 shows staining of human monocytes with 146B7, or with the control antibody, hIgG1. A clear red staining of the cytoplasm is observed after incubating the cells with 146B7, but not with the control antibody. Accordingly, 146B7 binds hIL-15 in monocytes and this binding is upregulated after stimulation with IFNγ. FIG. 11 also shows that IL-15 staining is primarily intracellular.

Example 10

Human Anti-IL-15 Antibody 146B7 Binds IL-15 in Tissues by Immunohistochemistry

Test Compounds

Human psoriatic skin—tissue samples were obtained after informed consent. Louise Villadsen, Department of Dermatology, Gentofte University Hospital, Copenhagen, Denmark.

Antibody 146B7 (batch no. MDX015), Medarex, Annandale, N.J., USA

Biotinylation of 146B7 and Human IG

N-hydroxysuccinimido-biotin (Sigma) was first diluted in DMSO (final dilution: 100 mg/ml) and then in 0.1 M $NaHCO_3$ (final dilution: 1 mg/ml, Sigma). Per 1 mg of antibody (diluted in 1 ml), 600 μl of biotin solution was added (dark, 2 hrs, RT). Antibody-biotin solution was dialysed in a Slide-a-lyzer™ dialysis cassette (10,000 MWCO, Pierce, Perbio Science, Netherlands) (ON, 4° C.) to remove unlabeled biotin. The following day, concentration of biotinylated antibodies was determined by spectrophotometry (Ultrospec 2100pro) at OD 280 nm.

Immunohistochemistry

Tissues were stored at −80° C. until assay. After thawing, tissue sections were fixated in acetone (10 min, RT) and air-dried. To block endogenous peroxidase activity, sections were incubated with 0.05% (v/v) hydrogen peroxide ($H_2O_2$) diluted in citric acid/phosphate buffer (pH 5.8, 20 min, RT). After washing with PBS-Tween 20 (PBST, 0.05% v/v), endogenous biotin activity was blocked according to the manufacturer's instructions (Biotin Blocking Kit, Vector Lab., DAKO). After washing with PBST, non-specific binding sites were blocked by incubating the tissue sections with 10% (v/v) human pooled AB-serum (CLB, Amsterdam, Netherlands) (30 min) in PBST. Serum was blotted off and sections were subsequently incubated with biotinylated primary antibody (146B7 or hIgG1) diluted in PBS containing 2% human AB serum for 60 minutes (RT). Sections were washed in PBST. After washing in PBST, all tissue sections were incubated with streptABComplex/HRP (DAKO; 1:100 diluted in PBS containing 2% human AB serum; 30 min, RT). After washing in PBST, the sections were incubated with 3-amino-9-ethylcarbazole (0.5 mg/ml) and $H_2O_2$ (0.01%), in sodium acetate buffer (50 mM, pH 4.9) for 10 minutes (RT), for the detection of HRP activity. Sections were washed with running tap water for 5 minutes, counterstained with haematoxylin (DAKO) for one minute, washed with running tap water for another 5 minutes, and finally embedded in faramount or glycergel (DAKO).

Results

Figure 12A:
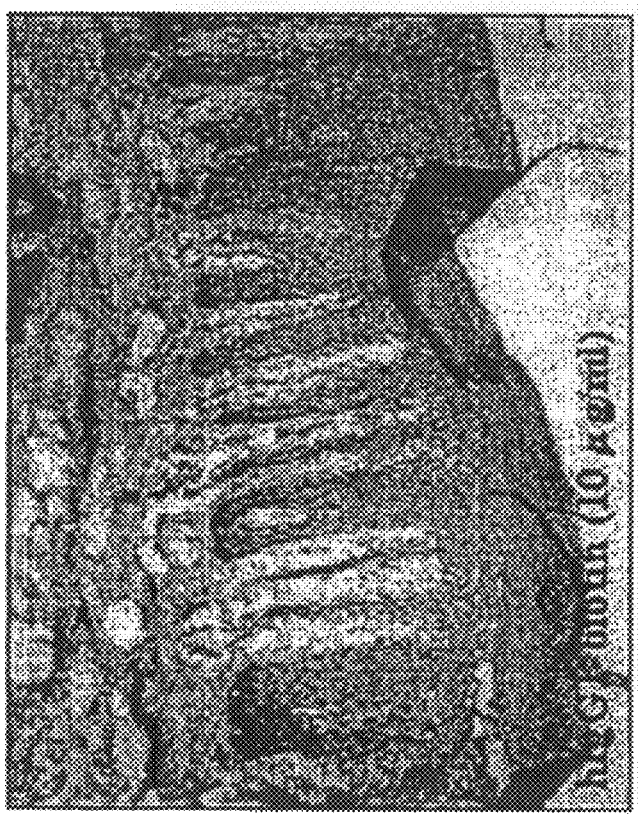
FIG. 12 shows binding of human psoriatic skin with 146B7 (panel B) or with the isotype control antibody (hIgG1) (panel A). Human psoriatic plaques were obtained from patients after informed consent, and stored at −80° C. until assay. Tissues were stained with biotinylated antibodies and visualized after activation of horse radish peroxidase.
Figure 12B:
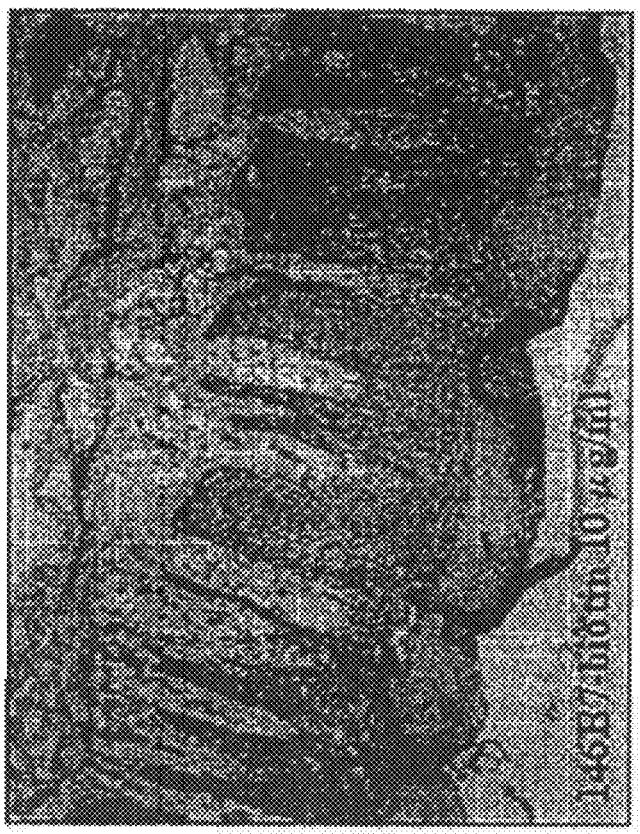

A clear cytoplasmic staining of keratinocytes in psoriatic skin was observed after staining tissue sections with 146B7, but not with the control antibody (FIG. 12; 146B7 stains IL-15-positive keratinocytes obtained from psoriatic plaques).

Example 11

Human Anti-IL-15 Antibody 146B7 Blocks IL-15 in SCID Mouse-Human Tissue Chimeras: Significant Inhibition of Inflammation in Both Arthritic and Psoriatic Tissue Test Compounds Synovial tissue—obtained form patients with juvenile rheumatoid arthritis, after informed consent; Alexei Grom, division of pediatric rheumatology, Children's Hospital Medical Center, Cincinnati, Ohio, USA.

Keratome biopsies—tissue samples were obtained after informed consent. Louise Villadsen, Department of Dermatology, Gentofte University Hospital, Copenhagen, Denmark.

Antibody 146B7 (batch no. MDX015), Medarex Inc., Annandale, N.J., USA for psoriasis experiments.

Antibody 146B7 (batch no. 15-00RDJW07), Medarex Inc., Annandale, N.J., USA for rheumatoid arthritis experiments.

Blocking IL-15 in SCID Mouse—Human Synovial Tissue Chimeras

Fresh synovial tissue samples were obtained from patients with juvenile rheumatoid arthritis after joint replacement surgery. Samples were collected in sterile conditions. Minced tissue fragments from the entire synovial tissue sample were thoroughly mixed to ensure homogeneity of each preparation. Minced tissues (2-4 grafts per animal; 100 mg per one site) were engrafted subcutaneously in the back of SCID/NOD mice (Jackson Laboratories). Each animal received 146B7 (500 µg, i.p.) or PBS on the day of graft implantation, and on post-implantation days 7, 14, and 21. Animals were sacrificed on day 28 post-implantation. Synovial grafts were excised and placed on formalin for H&E staining.

Quantification of H&E Staining of Tissues from SCID Mouse—Human Synovial Tissue Chimeras (Modified from Lehr et al. J. Histochem. Cytochem. 1997, 45, 1559)

After obtaining digital images (2600×2060, jpg) of sections obtained from SCID mouse—human synovial tissue chimeras using a X10 objective (Zeiss microscope; Axiovision software), data were computer-analysed, by use of Photoshop, version 6.0 (Adobe Systems, Mountain view, Calif.) and reduced to 1300×1300 pixels. Within each section six X10 fields were chosen so as to best reflect the overall staining of the tissue on the entire slide. After selection of all stained nuclei (magic wand on dark nucleus with tolerance 10), an optical density plot of the selected area was generated and the mean staining intensity was recorded (after selection of similar/image histogram command). Subsequently, the background was selected and staining was quantified (magic wand on background with tolerance 10). Staining intensity was calculated as the difference between nuclear staining and background staining. This was designated the cytochemical index with arbitrary units. Data are shown as mean and s.e.m. Data were analysed by Student's t-test.

Blocking IL-15 in SCID Mouse—Human Psoriatic Tissue Chimeras

Keratome biopsies were obtained from psoriatic plaques of two patients, divided and transplanted onto C.B-17 SCID (Jackson Laboratories) mice. Three weeks after transplantation mice received PBS (placebo), CsA (cyclosporine A) (Sandoz) at a dose of 10 mg/kg every second day for 15 days, or 146B7 at a dose of 20 mg/kg on day 1 and 10 mg/kg on days 8 and 15. One week after the last injection, mice were sacrificed, and a 4 mm punch biopsy was taken from each xenograft. Biopsies were fixed in formalin for paraffin embedding and stained in H&E (FIG. 15) and for Ki-67 nuclear antigen (FIG. 16).

Quantification of Immunohistochemical Staining of Tissues from SCID Mouse—Human Psoriatic Tissue Chimeras The H&E-stained sections were evaluated for epidermal thickness (µm), grade of parakeratosis (rated from 0-3), and number of inflammatory mononuclear cells in upper dermis. The sections stained for Ki-67 were evaluated for number of cycling keratinocytes/mm$^2$ section. Mean values for the 4 mice in each treatment group were calculated, and the data from each patient were summarised as mean and s.e.m.

SCID/RA Model

Figure 13A:
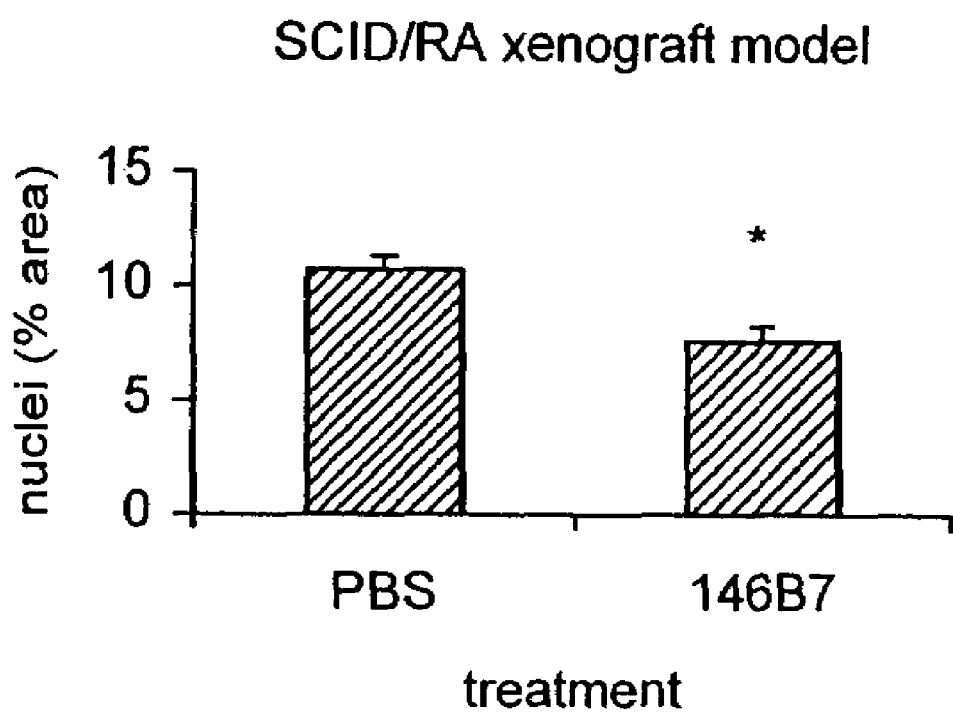
FIG. 13A is a graph showing the percentage of nucleated cells in rheumatoid arthritic tissue after treatment of SCID mice with 146B7 or with vehicle. Tissues were stained with haematoxilin and eosin (H&E) and analysed with Photo Shop version 6.0. Data are shown as mean and s.e.m. of nuclei (as percentage of total area) of mice after 146B7 treatment (n=4) or vehicle treatment (n=2).
Figure 13C:
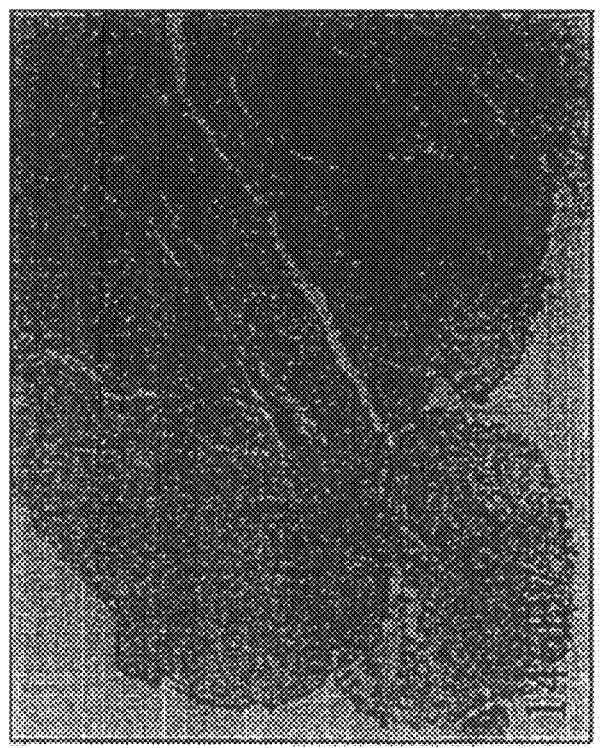
FIGS. 13B and 13C show a representative H&E staining of xenografted RA tissue in SCID mice, after treatment with 146B7 (FIG. 13C) or with PBS (FIG. 13B).
Figure 13B:
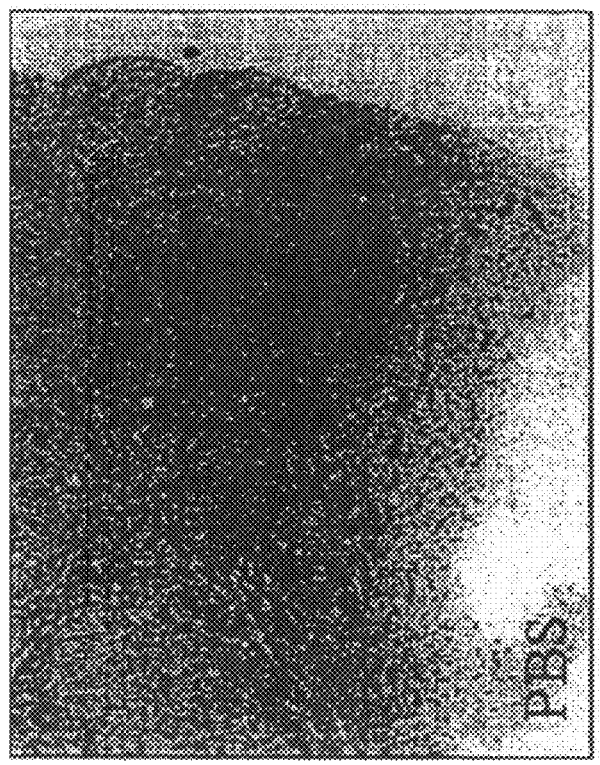
Figure 14A:
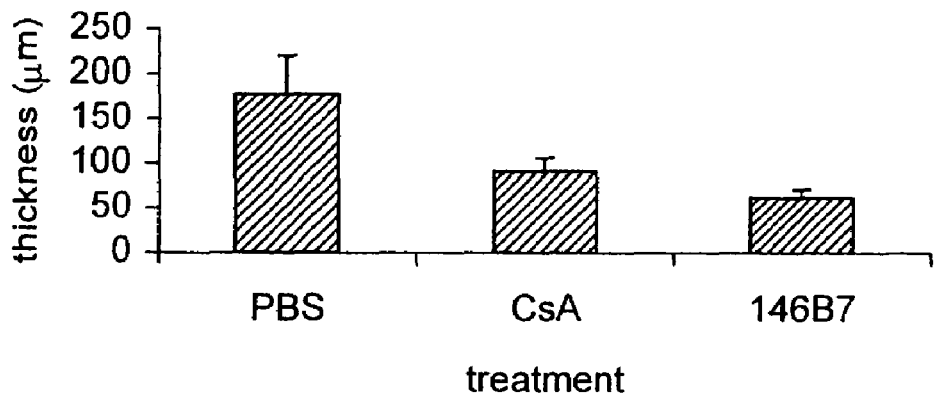
FIG. 14A shows the severity of psoriasis evaluated by epidermal thickness which was measured from the stratum corneum to the beginning of the rete pegs.
Figure 14B:
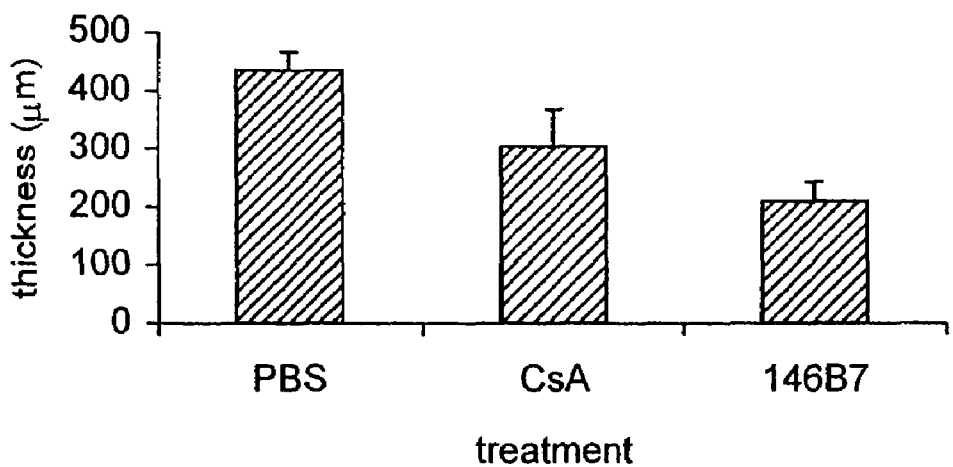
FIG. 14B shows the epidermal thickness which was measured from the stratum corneum to the deepest part of the rete pegs.
Figure 14C:
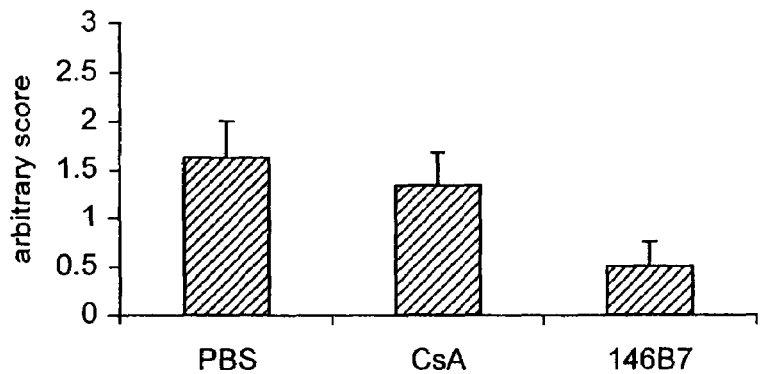
FIG. 14C shows the grade of parakeratosis.
Figure 14D:
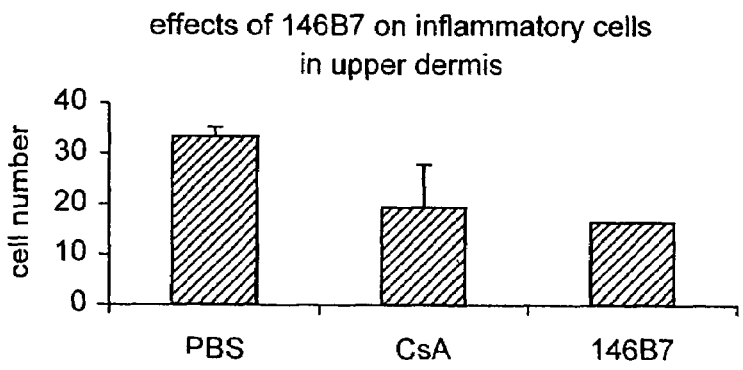
FIG. 14D shows the number of inflammatory mononuclear cells in upper dermis.
Figure 14E:
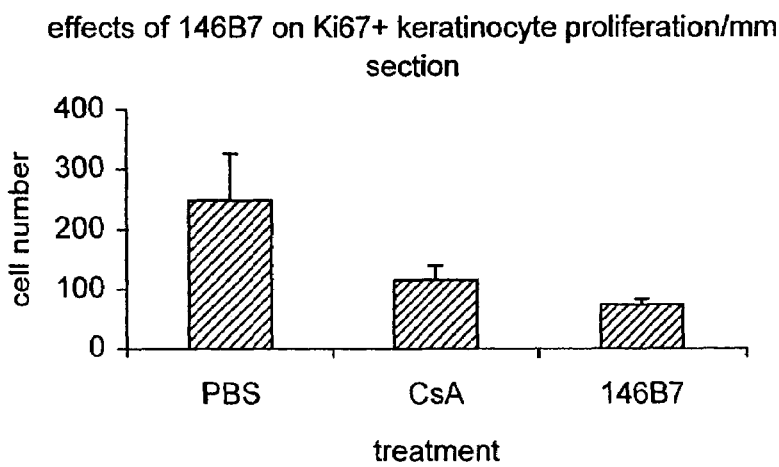
FIG. 14E shows the number of Ki-67+ cycling keratinocytes.

Microscopic observation of sections showed that the darkest stained nuclei belong to infiltrating cells. Therefore, the number of nuclei (measured as the relative surface area) are considered as a measure for infiltration. Injection of 146B7 reduces the number of infiltrating cells into inflamed synovial tissue, as compared to vehicle treatment (FIG. 13a, p<0.05). FIGS. 13B and 13C illustrate the effects of 146B7 (FIG. 13C) on infiltration of cells into xenografted synovial tissue, and show a reduction in number of cells with dark nuclei, as compared to vehicle treatment (FIG. 13B).

SCID/Psoriasis Model

FIG. 14 shows SCID/psoriasis mice treated with 146B7 or control treatment. Compared to the vehicle, PBS, injections of 146B7 reduced the severity of psoriasis evaluated by epidermal thickness when was measured from the stratum corneum to the beginning of the rete pegs (FIG. 14A): PBS (177.8$^\pm$42.2 µm), CsA (91.0$^\pm$15.2 µm), 146B7 (62.5$^\pm$9.1 µm). A reduction in thickness was also observed when was measured from the stratum corneum to the deepest part of the rete pegs (FIG. 14B): PBS (433.8$^\pm$32.1 µm), CsA (303.8$^\pm$62.9 µm) and 146B7 (208.0$^\pm$33.8 µm). Also, the grade of parakeratosis was reduced by 146B7 treatment (FIG. 14C): PBS (1.6$^\pm$0.4), CsA (1.3$^\pm$0.3), 146B7 (0.5$^\pm$0.3). Furthermore, 146B7 reduces the number of inflammatory mononuclear cells in upper dermis (FIG. 14D): PBS (33.3$^\pm$1.9 mononuclear cells), CsA (19.4-8.5), 146B7 (16.4-0.1). The expression of the human Ki-67 protein is strictly associated with cell proliferation. During interphase, the antigen can be exclusively detected within the nucleus, whereas in mitosis most of the protein is relocated to the surface of the chromosomes. The fact that the Ki-67 protein is present during all active phases of the cell cycle (G(1), S, G(2), and mitosis), but is absent from resting cells (G(0)), makes it an excellent marker for determining the so-called growth fraction of a given cell population. 146B7 reduces the number of Ki-67+ cycling keratinocytes (FIG. 14E): PBS (247.9±77.0), CsA (116.0±24.1), 146B7 (73.8±9.9).

Treatment with 146B7 inhibited the infiltration of inflammatory cells into inflamed tissue in human SCID models for rheumatoid arthritis. Furthermore, in SCID mice with engrafted human psoriatic plaques, treatment with 146B7 reduced the severity of psoriasis, as compared to treatment with CsA. Indeed, treatment with 146B7 resulted in a major reduction in inflammation, in epidermal thickness, in numbers of dividing keratinocytes, and in severity of parakeratosis in human/SCID mice.

Example 12

Human Anti-IL-15 Antibody 146B7 Recognizes Receptor-Bound IL-15

Test Compounds hIgG1—human control antibody (Sigma).

Antibody 146B7—Medarex Inc., Annandale, N.J., USA, MDX015.

Raji cells with constitutive expression of IL-15Rα (Martin Glennie, Tenovus Research Laboratory, Southampton General Hospital, Southampton, U.K.).

Biotinylation of 146B7 and Human IgG

N-hydroxysuccinimido-biotin (Sigma) was first diluted in DMSO (final dilution: 100 mg/ml) and then in 0.1 M NaHCO$_3$ (final dilution: 1 mg/ml, Sigma). Per 1 mg of antibody (diluted in 1 ml), 600 µl of biotin solution was added (dark, 2 hrs, RT). Antibody-biotin solution was dialysed in a Slide-a-lyzer™ dialysis cassette (10,000 MWCO, Pierce, Perbio Science, Netherlands) (overnight at 4° C.) to remove unlabeled biotin. The following day, concentration of biotinylated antibodies was determined by spectrophotometry (Ultrospec 2100pro) at OD 280 nm.

Binding of 146B7 to IL-15-IL-15Rα Complex by ELISA

After coating (overnight at room temperature) flat bottom microtiter plates (Greiner) with IL-15Rα (R&D systems, Minneapolis, Minn., USA), plates were incubated with PBS and chicken serum (2%, RT, 60 min). After washing in PBS (+0.05% Tween 20: PBST), plates were subsequently incubated with several dilutions of unlabeled IL-15 (50 µl, RT, immunex, Seattle, USA). After 10 minutes, biotinylated antibodies were added to the wells (50 µl) in different concentrations (90 minutes at room temperature). After washing in PBST, plates were incubated (60 minutes at room temperature) with streptavidin-poly-horseradish peroxidase (CLB, Amsterdam, Netherlands) diluted 1:10,000 in PBST-C (PBST and 2% chicken serum). Finally, plates were washed and subsequently incubated with ABTS (Azinobis-3-ethyl-benzthiazoline-sulphonic-acid, Roche Diagnostics, Mannheim, Germany) in ABTS buffer according to the manufacturer's protocol. Color reaction was stopped with 2% oxalic acid (50 µl). Binding was evaluated at 405 nm in an EL808 ELISA-reader (Bio-Tek Instruments, Winooski, Vt., USA).

Binding of 146B7 to IL-15-IL-15R Complex on Raji Cells

Raji cells are pre-incubated (20 minutes at 4° C.) with 10% human pooled AB serum (CLB, Amsterdam, Netherlands) in FACS buffer (PBS, 0.05% BSA, 0.02% $NaNO_3$). Raji cells ($1-2*10^5$ cells/ml) were put in the wells, and 50 µl of unlabeled IL-15 was added in several concentrations (diluted in FACS buffer with 10% human AB serum). After incubating the cells for 30 minutes (4° C.) and washing twice in FACS buffer, 50 µl of biotinylated antibodies (146B7 or hIgG1) was added to the wells (30 minutes at 4° C.). After washing twice in FACS buffer, 50 µl of streptavidin-phycoerythrin was added to each well (30 minutes at 4° C.). After washing twice in FACS buffer, cells were taken up in 200 µl of FACS buffer, and fluorescence intensity of at least 5000 cells per sample was determined after analysis by flow cytometry (FACS Calibur, Becton Dickinson) using CellQuest software. Data show the stimulation index (S.I.), which is calculated as follows:

$$S.I.=(\text{mean fluorescence positive staining})/(\text{mean fluorescence background staining})$$

Elisa

Figure 17:
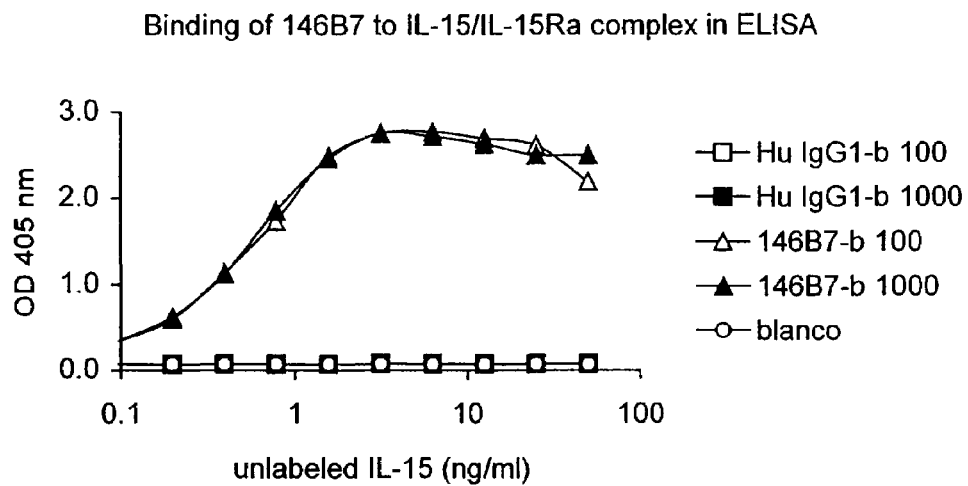
FIG. 17 is a graph showing the binding of antibody 146B7 to receptor-bound IL-15. Plates were coated with IL-15Rα and incubated with IL-15. After 10 minutes, biotinylated 146B7 was added to the wells. Binding of 146B7 to receptor-bound IL-15 was evaluated at 405 nm in an ELISA-reader.

Binding of 146B7 to IL-15/IL-15R complex in ELISA is shown in FIG. 17. Binding of 146B7 increases with increasing concentrations of IL-15 binding to its receptor. No effects were observed of binding of control antibody to IL-15 or to IL-15R.

Binding to IL-15R-Expressing Raji Cells

Figure 18:
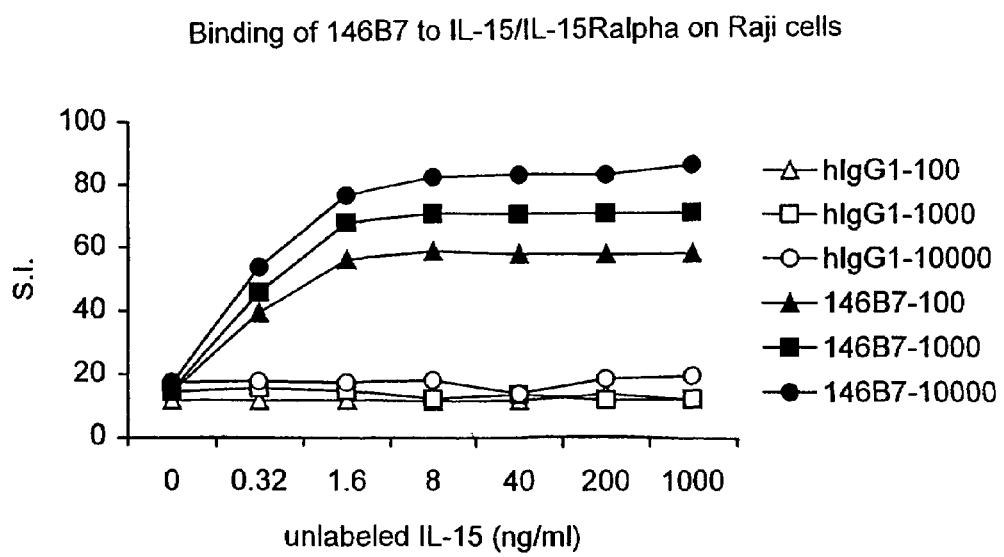
FIG. 18 is a graph showings the binding of antibody 146B7 to IL-15, after binding of IL-15 to its receptor expressed on Raji cells. After incubation of IL-15R-expressing Raji cells with IL-15, biotinylated 146B7 was added to the cells after 10 minutes. Binding of 146B7 to receptor-bound IL-15 was evaluated by FACS analysis.

Binding of 146B7 to IL-15/IL-15R complex on Raji cells is shown in FIG. 18. 146B7 binds to the IL-15/IL-15R complex in a dose-dependent manner. No binding of hIgG1 to the IL-15/IL-15R complex on Raji cells was observed (FIG. 18).

146B7 is able to bind IL-15 after binding of this cytokine to its receptor. 146B7 binds to an epitope on IL-15 that is not involved in binding to the receptor.

REFERENCES

Bathon J. M., Martin R. W., Fleischmann R. M., Tesser J. R., Schiff M. H., Keystone E. C., Genovese M. C., Wasko M. C., Moreland L. W., Weaver A. L., Markenson J. and Finck B. K. (2000) A comparison of etanercept and methotrexate in patients with early rheumatoid arthritis. N Engl J Med 343, 1586-93.

Fehniger T. A. and Caligiuri M. A. (2001) Interleukin 15: biology and relevance to human disease. Blood 97: 14-28.

Fishwild D. M., O'Donnell S. L., Bengoechea T., Hudson D. V., Harding F., Bernhard S. L., Jones D., Kay R. M., Higgins K. M., Schramm S. R. and Lonberg N. (1996) High-avidity human IgGk monoclonal antibodies from a novel strain of minilocus transgenic mice. Nature biotechn. 14: 845-51.

Gillis S., Ferm M. M., Ou W. and Smith K. A. (1978) T cell growth factor: parameters of production and a quantitative microassay for activity. J Immunol 120, 2027-32.

Kennedy M. K., et al. (2000) Reversible defects in natural killer and memory CD8 T cell lineages in IL-15 deficient mice. J. Exp. Med. 191: 771-80

Kirman I., Vainer B. and Nielsen O. H. (1998) Interleukin-15 and its role in chronic inflammatory diseases. Inflamm Res 47, 285-9.

Klippel J. H. (2000) Biologic therapy for rheumatoid arthritis. N Engl J Med 343, 1640-1.

Köhler G. and Milstein C. (1975) Continuous cultures of fused cells secreting antibody of predefined specificity. Nature 256: 495-7.

Liu C. C., Perussia B. and Young J. D. (2000) The emerging role of IL-15 in NK-cell development. Immunol Today 21, 113-6.

Lovell D. J., Giannini E. H., Reiff A., Cawkwell G. D., Silverman E. D., Nocton J. J., Stein L. D., Gedalia A., Ilowite N. T., Wallace C. A., Whitmore J. and Finck B. K. (2000) Etanercept in children with polyarticular juvenile rheumatoid arthritis. Pediatric Rheumatology Collaborative Study Group. N Engl J Med 342, 763-9.

Maini R. N. and Taylor P. C. (2000) Anti-cytokine therapy for rheumatoid arthritis. Annu Rev Med 51, 207-29.

McInnes I. B., al-Mughales J., Field M., Leung B. P., Huang F. P., Dixon R., Sturrock R. D., Wilkinson P. C. and Liew F. Y. (1996) The role of interleukin-15 in T-cell migration and activation in rheumatoid arthritis. Nat Med 2, 175-82.

McInnes I. B., Leung B. P., Sturrock R. D., Field M. and Liew F. Y. (1997) Interleukin-15 mediates T cell-dependent regulation of tumor necrosis factor-alpha production in rheumatoid arthritis. Nat Med 3, 189-95.

McInnes I. B. and Liew F. Y. (1998) Interleukin 15: a proinflammatory role in rheumatoid arthritis synovitis. Immunol Today 19, 75-9.

Oppenheimer-Marks, et al. (1997) J. Clin. Investig. 101:1261-72. Pettit D. K., Bonnert T. P., Eisenman J., Srinivasan S., Paxton R., Beers C., Lynch D., Miller B., Yost J., Grabstein K. H. and Gombotz W. R. (1997) Structure-function studies of interleukin 15 using site-specific mutagenesis, polyethylene glycol conjugation, and homology modeling. J Biol Chem 272, 2312-8.

Ruchatz, et al. (1998) J. Immunol. 160:5654-60.

Waldmann T., Tagaya Y. and Bamford R. (1998) Interleukin-2, interleukin-15, and their receptors. Int Rev Immunol 16, 205-26.

Waldmann T. A., Dubois S, and Tagaya Y. (2001) Contrasting Roles of IL-2 and IL-15 in the Life and Death of Lymphocytes. Implications for Immunotherapy. Immunity 14, 105-110.

Waldmann T. A. and Tagaya Y. (1999) The multifaceted regulation of interleukin-15 expression and the role of this cytokine in NK cell differentiation and host response to intracellular pathogens. Annu Rev Immunol 17, 19-49.

Equivalents

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

All publications, patents, and pending patent applications referred to herein are hereby incorporated by reference in their entirety.

---

We claim:

1. A method of treating psoriasis caused by the proinflammatory effects of human IL-15, comprising administering to a subject a monoclonal antibody or antigen binding portion thereof which binds to human IL-15, in an amount effective to treat psoriasis, wherein the heavy chain variable region of the antibody comprises the amino acid sequence set forth in SEQ ID NO:2.

2. A method of treating psoriasis caused by the proinflammatory effects of human IL-15, comprising administering to a subject a monoclonal antibody or antigen binding portion thereof which binds to human IL-15, in an amount effective to treat psoriasis, wherein the light chain variable region of the antibody comprises the amino acid sequence set forth in SEQ ID NO:4.

3. A method of treating psoriasis caused by the proinflammatory effects of human IL-15, comprising administering to a subject a monoclonal antibody or antigen binding portion thereof which binds to human IL-15, in an amount effective to treat psoriasis, wherein the heavy and light chain variable regions of the antibody comprise the amino acid sequences set forth in SEQ ID NO:2 and SEQ ID NO:4, respectively.

4. A method of treating psoriasis caused by the proinflammatory effects of human IL-15, comprising administering to a subject a monoclonal antibody or antigen binding portion thereof in an amount effective to treat psoriasis, wherein the antibody binds an epitope on human IL-15 recognized by an antibody comprising heavy chain and human light chain variable regions comprising the amino acid sequences set forth in SEQ ID NO:2 and SEQ ID NO:4, respectively.

5. The method of claim 4, wherein the antibody inhibits IL-15-induced TNFα production or T cell proliferation.

6. The method of claim 4, wherein the antibody binds to human IL-15 with a dissociation equilibrium constant ($K_D$) of below $10^{-7}$ M as determined by surface plasmon resonance (SPR) technology using recombinant human IL-15 as the analyte and the antibody as the ligand.

7. The method of claim 4, wherein the antibody binds to an epitope located on the β-chain or the γ-chain interacting domain of human IL-15.

8. The method of claim 4, wherein the antibody binds to receptor-bound human IL-15.

9. The method of claim 4, wherein the antibody is selected from the group consisting of an IgG1, IgG2, IgG3, IgG4, IgM, IgA1, IgA2, IgAsec, IgD, and IgE antibody.

10. The method of claim 4, wherein the antibody is an IgG1 antibody.

11. The method of claim 4, wherein the antibody comprises a variable region from an IgG1 heavy chain and a variable region from a kappa light chain.

12. The method of claim 4, wherein the antibody is a Fab fragment or a single chain antibody.

13. The method of claim 4, wherein the antibody is administered in the form of a composition further comprising a pharmaceutically acceptable carrier.

\* \* \* \* \*